(12) United States Patent
Schlachter et al.

(10) Patent No.: US 11,918,705 B2
(45) Date of Patent: *Mar. 5, 2024

(54) ELECTRON BEAM IRRADIATED OSTEOINDUCTIVE BONE IMPLANT

(71) Applicant: Warsaw Orthopedic, Inc., Warsaw, IN (US)

(72) Inventors: Kelly W. Schlachter, Mason, TN (US); Erick Vasquez, Memphis, TN (US); Daniel A. Shimko, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 109 days.

This patent is subject to a terminal disclaimer.

(21) Appl. No.: 17/403,314

(22) Filed: Aug. 16, 2021

(65) Prior Publication Data

US 2021/0402060 A1    Dec. 30, 2021

Related U.S. Application Data

(63) Continuation of application No. 15/008,676, filed on Jan. 28, 2016, now Pat. No. 11,090,411.

(51) Int. Cl.
| | |
|---|---|
| A61L 27/36 | (2006.01) |
| A61L 2/08 | (2006.01) |
| A61L 27/54 | (2006.01) |

(52) U.S. Cl.
CPC ........... *A61L 27/3691* (2013.01); *A61L 2/087* (2013.01); *A61L 27/3608* (2013.01); *A61L 27/365* (2013.01); *A61L 27/54* (2013.01); *A61L 2202/11* (2013.01); *A61L 2202/21* (2013.01); *A61L 2300/412* (2013.01); *A61L 2430/02* (2013.01)

(58) Field of Classification Search
CPC .. A61L 27/3691; A61L 2/087; A61L 27/3608; A61L 27/365; A61L 27/54; A61L 2202/11; A61L 2202/21; A61L 2300/412; A61L 2430/02
See application file for complete search history.

(56) References Cited

U.S. PATENT DOCUMENTS

| | | | |
|---|---|---|---|
| 5,531,791 | A | 7/1996 | Wolfinbarger, Jr. |
| 7,498,041 | B2 | 3/2009 | Masinaei et al. |
| 7,811,608 | B2 | 10/2010 | Kay et al. |
| 7,815,682 | B1 | 10/2010 | Peterson et al. |
| 2002/0120338 | A1 | 8/2002 | Boyer, II et al. |
| 2003/0009235 | A1 | 1/2003 | Manrique et al. |
| 2003/0114936 | A1 | 6/2003 | Sherwood et al. |
| 2003/0143258 | A1 | 7/2003 | Knaack et al. |
| 2003/0167092 | A1 | 9/2003 | Foley |
| 2004/0097612 | A1 | 5/2004 | Rosenberg et al. |
| 2005/0021142 | A1 | 1/2005 | Ganz et al. |
| 2005/0085922 | A1 | 4/2005 | Shappley et al. |
| 2006/0233851 | A1 | 10/2006 | Simon et al. |
| 2006/0280803 | A1 | 12/2006 | Kumar et al. |
| 2006/0293757 | A1 | 12/2006 | McKay et al. |
| 2007/0098756 | A1 | 5/2007 | Behnam |
| 2007/0248575 | A1 | 10/2007 | Connor et al. |
| 2008/0114465 | A1 | 5/2008 | Zanella et al. |
| 2008/0281431 | A1 | 11/2008 | Missos |
| 2009/0130173 | A1 | 5/2009 | Behnam et al. |
| 2009/0155378 | A1 | 6/2009 | Behnam et al. |
| 2009/0192474 | A1 | 7/2009 | Wei et al. |
| 2009/0253810 | A1 | 10/2009 | Katz |
| 2009/0319045 | A1 | 12/2009 | Truncale et al. |
| 2010/0042216 | A1 | 2/2010 | Kilpela et al. |
| 2010/0129415 | A1 | 5/2010 | Kinnane et al. |
| 2010/0268232 | A1 | 10/2010 | Betz et al. |
| 2010/0286783 | A1 | 11/2010 | Lechmann et al. |
| 2011/0144766 | A1 | 6/2011 | Kale et al. |
| 2011/0182963 | A1 | 7/2011 | McKay |
| 2014/0212471 | A1 | 7/2014 | Drapeau et al. |
| 2015/0306278 | A1 | 10/2015 | McKay |
| 2016/0136329 | A1* | 5/2016 | Schlachter ........ B01F 33/50112 264/28 |

FOREIGN PATENT DOCUMENTS

| | | |
|---|---|---|
| JP | 2009-534125 A | 9/2009 |
| JP | 2009534125 A | 9/2009 |
| WO | 2007/124302 A2 | 11/2007 |
| WO | 2008157492 | 12/2008 |
| WO | 2008157492 A2 | 12/2008 |

OTHER PUBLICATIONS

Japan Patent Office—Notification of Reasons for Rejection (Office Action), Japanese Patent App. No. 2021-179470, dated Dec. 9, 2022.
Qing-Qing Qiu et al: "Effects of e-beam radiation, storage, and hydration on osteoinductivity of DBM/AM composite", Journal of Biomedical Materials Research . Part B: Applied Biomaterials, vol. 91B, No. 1, Oct. 1, 2009 (Oct. 1, 2009), pp. 401-408.
Office Action dated Oct. 5, 2021 by the European Patent Office in corresponding European patent application No. 20188377.4.
Edwards et al., Osteoinduction of Human Demineralized Bone: Characterization in a Rat Model, Clinical Orthopaedics and Related Research, No. 357, pp. 219-228, 1998 Lippincott Williams and Wilkins, 10 pages.
Qui et al., Effects of y-irridation, storage and hydration on osteoinductivity of DBM and DBM/AM composite, Department of Development, LifeCell Corporation, One Millinnium Way, Branchburg, NJ 08876, 2008 Journal of Biomedical Materials Research Part A, 7 pages.

(Continued)

*Primary Examiner* — David W Berke-Schlessel
*Assistant Examiner* — Susan E. Fernandez
(74) *Attorney, Agent, or Firm* — Sorell, Lenna & Schmidt, LLP

(57) ABSTRACT

A method of making an electron beam irradiated osteoinductive implant is provided. The method comprises exposing an osteoinductive implant containing demineralized bone matrix (DBM) fibers to electron beam radiation at a dose of from about 10 kilograys to 100 kilograys for a period of time. The electron beam irradiation reduces microorganisms in the osteoinductive implant, and the electron beam irradiated osteoinductive implant retains osteoinductive properties. Methods of implantation and an irradiated osteoinductive implant are also disclosed.

10 Claims, 14 Drawing Sheets

(56) References Cited

OTHER PUBLICATIONS

Qui et al., Effects of E-Beam Radiation, Storage, and Hydration on Osteoinductivity of DBM/AM Composite, LifeCell Corporation, Branchburg, NJ 08876, 2009 Journal of Biomedical Materials Research Part B, Applied Biomaterials, 8 pages.

The Effects of E-Beam Sterilization on the Performance of JRF StimuBlast(tm) Demineralized Bone Matrix, Arthrex Research and Development, Arthrex, Inc., 2011, 2 pages.

The Newspaper of the Korean Dental Association, New Product CGBIO Bone graft material 'CGDBM100', Sep. 21, 2009, No. 1774, p. 43. Retrieved from the Internet<URL:http://dailydental.co.kr/data/pdf/20090921_1774/flashbook.html>. See the article box of the upper left side on p. 43.

International Search Report and Written Opinion for PCT/2017/014024 the counterpart application dated Apr. 25, 2017, 15 pages.

The Newspaper of the Korean Dental Association. New Product CGBIO Bone Graft Material 'CGDBM100'. Sep. 21, 2009. No. 1774, p. 43. Retrieved from the internet at <URL: http://dailydental.co.kr/data/pdf/20090921_1774/flashbook.html>. Article box in upper left corner of p. 43.

Arthrex's StimuBlastTM DBM website https://www.arthrex.com/hand-wrist/stimublast-demineralized-bone-matrix visited Feb. 4, 2019.

International Search Report and Written Opinion of the International Searching Authority (ISA/KR) dated Apr. 25, 2017 in International Appl. No. PCT/US2017/014025 for Electron Beam Irradiated Osteoinductive Bone Implant filed on Jan. 19, 2017.

European Search Report dated Aug. 6, 2019, issued by the European Patent Office in EP Appl. No. 17744706.7 for Electron Beam Irradiated Osteoinductive Bone Implant filed on Jan. 19, 2017.

Qing-Qing Qui et al: "Effects of e-beam radiation, storage, and hydration on osteoinductivity of DBM/AM composite" Journal of Biomedical Materials Research. Part B: Applied Biomaterials, vol. 91B, No. 1. Oct. 1, 2009 (Oct. 1, 2009), pp. 401-408, XP055609748, US ISSN: 1552-4973, DOI: 10.1002/jbm.b.31415.

The Newspaper of Korean Dental Association, New Product CGBIO Bone graft material 'CGDBM100', Sep. 21, 2009, No. 1774, p. 43. Retrieved from the Internet<URL:http://dailydental.co.kr/date/pdf/20090921_1774/flashbook.html>.

Qing-Qing, et al. Effects of E-Beam Radiation, Storage, and Hydration on Osteoinductivity of DBM/AM Composite. Journal of Biomedical Materials Research Part B. Applied Biomaterials, pp. 401-408.

Office Action issued by the China National IP Administration dated Sep. 30, 2020 in corresponding Chinese Patent Application No. 201780007858.2 for Electron Beam Irradiated Osteoinductive Bone Implant.

Office Action issued by the Japan Patent Office dated Sep. 29, 2020 in corresponding Japanese Patent Application No. 2018-539403.

Extended European Search Report dated Oct. 19, 2020 issued by the European Patent Office in corresponding European Patent Application No. 20188377.4.

* cited by examiner

ELECTRON BEAM IRRADIATED OSTEOINDUCTIVE BONE IMPLANT

BACKGROUND

It is estimated that more than half a million bone grafting procedures are performed in the United States annually with a cost over $2.5 billion. These numbers are expected to double by 2020. In addition, the U.S. market for osteobiologics has become very crowded and competitive. Hospitals are placing significant pressure on pricing while still demanding high performing products. Pricing is also a significant barrier when entering emerging markets such as Latin America, China, Middle East, etc.

Both natural bone and bone substitutes have been used as graft materials. Natural bone may be autograft or allograft. Bone substitutes include natural or synthetic materials such as collagen, silicone, acrylics, calcium phosphate, calcium sulfate, or the like. There are at least three ways in which a bone graft can help repair a defect. The first is osteogenesis, the formation of new bone within the graft by the presence of bone-forming cells called osteoprogenitor cells. The second is osteoinduction, a process in which molecules contained within the graft (e.g., bone morphogenic proteins and other growth factors) convert progenitor cells into bone-forming cells. The third is osteoconduction, a physical effect by which a matrix often containing graft material acts as a scaffold on which bone and cells in the recipient are able to form. The scaffolds promote the migration, proliferation and differentiation of bone cells for bone regeneration.

Demineralized bone matrix (DBM) has been shown to exhibit the ability to induce and/or conduct the formation of bone. It is therefore desirable to implant and maintain demineralized bone matrix at a site which bone growth is desired. Bone fiber based-demineralized bone matrices for implantation exhibit improvements in mechanical properties, including cohesiveness, fiber length, fiber diameter or width, fiber aspect ratio, or a combination of multiple variables.

GRAFTON® DBM demineralized bone fiber (DBF) is a high performing, carrier free, low moisture bone graft containing human DBM fibers, and processed aseptically to preserve osteoinductive potential. Aseptic processing requires extensive prescreening of donors, strict environmental controls and still may not meet all of the requirements for every market.

All radiation stems from ionizing radiation that can originate either from a radioactive source or from highly accelerated electrons. For medical radiotherapeutical or engineering purposes, the most common form of radiation involves photons, with energies up to kiloelectronvolts (KeV) and megaelectronvolts (MeV) and electrons with energies in the range between 4 and 15 MeV. In an X-ray tube, the cathode produces electrons by thermionic emission and acts as an electron source, with these electrons impinging on the positively charged anode after being accelerated in a strong electric field. The kinetic energy of the electrons is converted into X-radiation and then bremsstrahlung upon deceleration. The anode is composed of a high atomic-number material with a large bremsstrahlung cross-section and a high probability for producing bremsstrahlung, with about 99% of the kinetic energy of the electrons striking the anode transformed into thermal energy.

Charged particles produce electromagnetic radiation when they interact with matter, which is emitted as a characteristic line spectrum with energies typical for the emitting element, as well as bremsstrahlung with a continuous spectrum. Because of their large elm (charge divided by mass) ratio, which is much greater than the elm ratio for other charged particles like protons, deuterons or heavier ions, electrons produce significantly more bremsstrahlung. For commercial use, certain characteristics for an accelerator are its electron energy and average beam power. Industrial electron accelerators are usually classified according to their energy range, which is classified as low (80-300 keV), medium (300 keV-5 MeV), and high (above 5 MeV).

Electron beam processing or electron beam irradiation (EBI) is a process that involves using electrons, usually of high energy, to treat an object for a variety of purposes at various temperatures and under a nitrogen atmosphere. EBI is also used to treat products with a high-energy electron beam accelerator which utilizes an on-off technology with a common design similar to that of a cathode ray television. Electron energies typically fall within the keV to MeV ranges, depending on the depth of penetration required. The basic components of a typical electron beam processing device are an electron gun, dose chamber, magnet, emitter, grid, anode, and deflection coil. The electron gun is used to generate and accelerate the primary beam, while the magnetic optical focusing lens and deflection coil are used for controlling the way in which the electron beam impinges on a graft. The cathode emitter is a source of thermally-emitted electrons that are both accelerated and shaped into a collimated beam by the electrostatic field geometry established by the grid and anode. The electron beam then emerges from the gun assembly through an exit hole in the ground-plane anode with energy equal to the value of the negative high voltage being applied to the cathode. This use of a direct high voltage to produce a high-energy electron beam allows the conversion of input AC power to beam power at greater than 95% efficiency, making electron beam material processing a highly energy-efficient technique. After exiting the gun, the beam passes through an electromagnetic focusing lens and magnetic deflection coil system. This focusing lens is used for producing either a focused or de-focused beam spot on the graft, while the deflection coil is used to either position the beam spot on a stationary location or provide some form of oscillatory motion.

EBI technology has been used in the engineering and manufacturing industry, mainly for product modifications. The first modification is the cross-linking of polymer-based products to improve their mechanical, thermal, chemical properties. The second purpose is for degradation, often used in the recycling of materials. The third purpose is for the sterilization of medical and pharmaceutical goods.

For microbiological sterilization, EBI has the ability to break the DNA chains of living organisms, such as bacteria, resulting in microbial death and rendering the space they inhabit sterile. EBI has already been used for the sterilization of medical products, the development of aseptic packaging materials for foods, as well as for disinfectants. EBI's sterilization effect can also be applied in biomaterials such as bone grafts. For sterilization, EBI has significant advantages over other methods of sterilization currently in use. The process is quick, reliable, and compatible with most materials, and does not require any period of quarantine following processing. For some materials and products that are sensitive to oxidative effects, the radiation tolerance levels for EBI may be slightly higher than for gamma exposure. This is due to the higher dose rates and shorter exposure times of EBI, which have been shown to reduce the degradative effects of oxygen.

As a means of disinfection for pathogens, EBI could replace antiquated and environmentally unfriendly methods such as fumigation and chemical dipping. It has been previously proposed that electron beam has a detrimental effect on the osteoinductive potential of demineralized bone products since it destroys microorganisms by damaging DNA chains and also partially destroys other biologic components, such as natural formed proteins (collagen, growth factors, etc.

SUMMARY

A method of making an electron beam irradiated osteoinductive implant is provided. The method comprising: exposing an osteoinductive implant containing demineralized bone matrix (DBM) fibers to electron beam radiation at a dose of from about 10 kilograys to 100 kilograys for a period of time to reduce microorganisms in the osteoinductive implant and to obtain the electron beam irradiated osteoinductive implant, wherein the electron beam irradiated osteoinductive implant retains osteoinductive properties.

A method of treating a bone cavity is provided. The method comprising: implanting an osteoinductive implant into the bone cavity, the osteoinductive implant being irradiated with electron beam radiation at a dose of from about 10 kilograys to 100 kilograys for a period of time to reduce microorganisms in the osteoinductive implant, the osteoinductive implant containing demineralized bone matrix (DBM) fibers and being free of a carrier.

In some embodiments, an osteoinductive implant is provided. The osteoinductive implant comprises demineralized bone matrix (DBM) fibers that are free from a carrier. The osteoinductive implant is irradiated with electron beam radiation at a dose of from about 10 kilograys to 100 kilograys for a period of time to reduce microorganisms in the osteoinductive implant.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

Figure 1:
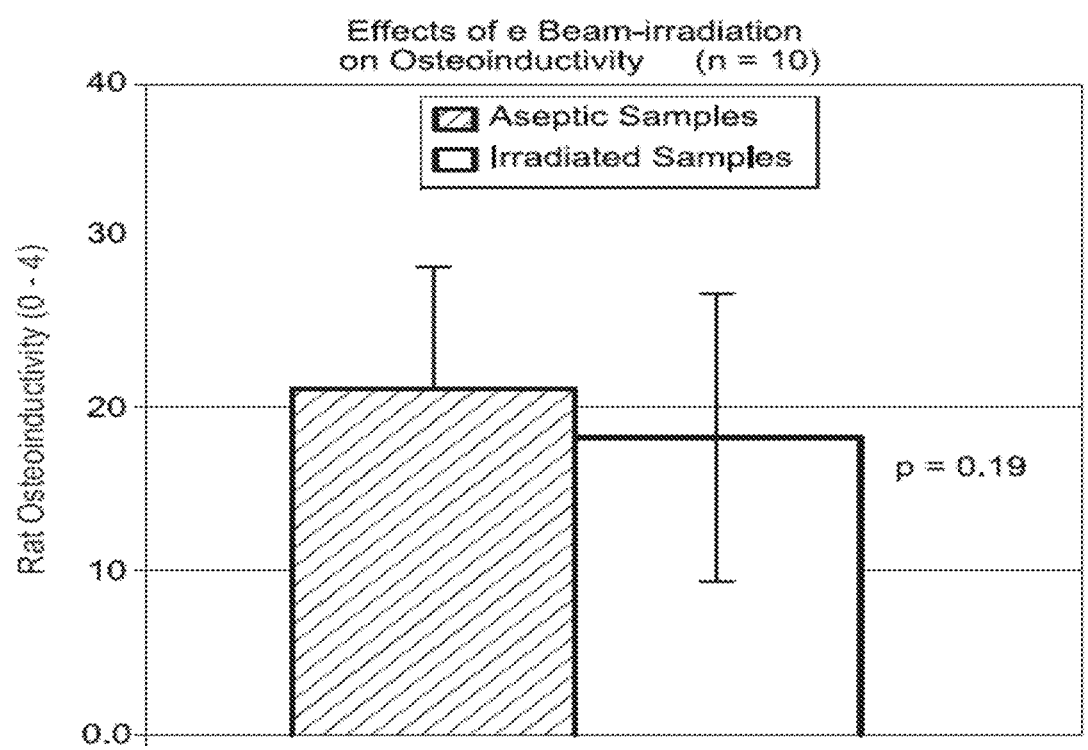
FIG. 1 depicts the effects of e-beam irradiation on the osteoinductivity of an osteoimplant in a rat.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of promoting an understanding of the principles of the disclosure, reference will now be made to certain embodiments and specific language will be used to describe the same. It will nevertheless be understood that no limitation of the scope of the disclosure is thereby intended, such alterations and further modifications in the illustrated device, and such further applications of the principles of the disclosure as described herein being contemplated as would normally occur to one skilled in the art to which the disclosure relates.

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present application. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations; the numerical representations are as precise as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Additionally, unless defined otherwise or apparent from context, all technical and scientific terms used herein have the same meanings as commonly understood by one of ordinary skill in the art to which this disclosure belongs.

Unless explicitly stated or apparent from context, the following terms are phrases have the definitions provided below:

Definitions

It is noted that, as used in this specification and the appended claims, the singular forms "a," "an," and "the," include plural referents unless expressly and unequivocally limited to one referent. Thus, for example, reference to "an allograft" includes one, two, three or more allografts.

The term "biodegradable" includes that all or parts of the carrier and/or implant will degrade over time by the action of enzymes, by hydrolytic action and/or by other similar mechanisms in the human body. In various embodiments, "biodegradable" includes that the carrier and/or implant can break down or degrade within the body to non-toxic components after or while a therapeutic agent has been or is being released. By "bioerodible" it is meant that the carrier and/or implant will erode or degrade over time due, at least in part, to contact with substances found in the surrounding tissue, fluids or by cellular action.

The term "mammal" refers to organisms from the taxonomy class "mammalian," including but not limited to humans, other primates such as chimpanzees, apes, orangutans and monkeys, rats, mice, cats, dogs, cows, horses, etc.

A "therapeutically effective amount" or "effective amount" is such that when administered, the drug (e.g., growth factor) results in alteration of the biological activity, such as, for example, promotion of bone, cartilage and/or other tissue (e.g., vascular tissue) growth, inhibition of inflammation, reduction or alleviation of pain, improvement in the condition through inhibition of an immunologic response, etc. The dosage administered to a patient can be as single or multiple doses depending upon a variety of factors, including the drug's administered pharmacokinetic properties, the route of administration, patient conditions and characteristics (sex, age, body weight, health, size, etc.), extent of symptoms, concurrent treatments, frequency of treatment and the effect desired. In some embodiments the implant is designed for immediate release. In other embodiments the implant is designed for sustained release. In other embodiments, the implant comprises one or more immediate release surfaces and one or more sustained release surfaces.

The terms "treating" and "treatment" when used in connection with a disease or condition refer to executing a protocol that may include a bone repair procedure, where the bone implant and/or one or more drugs are administered to a patient (human, other normal or otherwise or other mammal), in an effort to alleviate signs or symptoms of the disease or condition or immunological response or fill the bone cavity. Alleviation can occur prior to signs or symptoms of the disease or condition appearing, as well as after their appearance. Thus, treating or treatment includes preventing or prevention of disease or undesirable condition. In addition, treating, treatment, preventing or prevention do not require complete alleviation of signs or symptoms, does not require a cure, and specifically includes protocols that have only a marginal effect on the patient.

The term "bone," as used herein, refers to bone that is cortical, cancellous or cortico-cancellous of autogenous, allogenic, xenogenic, or transgenic origin.

The term "allograft" refers to a graft of tissue obtained from a donor of the same species as, but with a different genetic make-up from, the recipient, as a tissue transplant between two humans.

The term "autologous" refers to being derived or transferred from the same individual's body, such as for example an autologous bone marrow transplant.

The term "osteoconductive," as used herein, refers to the ability of a non-osteoinductive substance to serve as a suitable template or substance along which bone may grow.

The term "osteoinductive," as used herein, refers to the quality of being able to recruit cells from the host that have the potential to stimulate new bone formation. Any material that can induce the formation of ectopic bone in the soft tissue of an animal is considered osteoinductive.

The term "osteoinduction" refers to the ability to stimulate the proliferation and differentiation of pluripotent mesenchymal stem cells (MSCs). In endochondral bone formation, stem cells differentiate into chondroblasts and chondrocytes, laying down a cartilaginous extracellular matrix (ECM), which subsequently calcifies and is remodeled into lamellar bone. In intramembranous bone formation, the stem cells differentiate directly into osteoblasts, which form bone through direct mechanisms. Osteoinduction can be stimulated by osteogenic growth factors, although some ECM proteins can also drive progenitor cells toward the osteogenic phenotype.

The term "osteoconduction" refers to the ability to stimulate the attachment, migration, and distribution of vascular and osteogenic cells within the graft material. The physical characteristics that affect the graft's osteoconductive activity include porosity, pore size, and three-dimensional architecture. In addition, direct biochemical interactions between matrix proteins and cell surface receptors play a major role in the host's response to the graft material.

The term "osteogenic" refers to the ability of a graft material to produce bone independently. To have direct osteogenic activity, the graft must contain cellular components that directly induce bone formation. For example, an allograft seeded with activated MSCs would have the potential to induce bone formation directly, without recruitment and activation of host MSC populations. Because many osteoconductive allografts also have the ability to bind and deliver bioactive molecules, their osteoinductive potential will be greatly enhanced.

The term "osteoimplant," as used herein, refers to any bone-derived implant prepared in accordance with the embodiments of this disclosure and, therefore, is intended to include expressions such as a bone graft.

The term "Osteoinductivity score" refers to a score ranging from 0 to 4 as determined according to the method of Edwards et al. or an equivalent calibrated test. "Osteoinduction of Human Demineralized Bone: Characterization in a Rat Model," Edwards, Clinical Orthopaedics & Rel. Res., 357:219-228, December 1998. In the method of Edwards et al., a score of "0" represents no new bone formation; "1" represents 1%-25% of implant involved in new bone formation; "2" represents 26-50% of implant involved in new bone formation; "3" represents 51%-75% of implant involved in new bone formation; and "4" represents >75% of implant involved in new bone formation. In most instances, the score is assessed 28 days after implantation. However, the osteoinductivity score may be obtained at earlier time points such as 7, 14, or 21 days following implantation. In these instances it may be desirable to include a normal DBM control such as DBM powder without a carrier, and if possible, a positive control such as BMP. Occasionally osteoinductivity may also be scored at later time points such as 40, 60, or even 100 days following implantation. "Percentage of osteoinductivity" refers to an osteoinductivity score at a given time point expressed as a percentage of activity, of a specified reference score. Osteoinductivity may be assessed in an athymic rat or in a human. Generally, as discussed herein, an osteoinductive score is assessed based on osteoinductivity in an athymic rat. The osteoinductive implant of the current application retains osteoinductive potency even after e-beam irradiation. There is a slight decrease in osteoinductivity after e-beam irradiation by from about 1% to about 20% when compared to aseptic processing where no e-beam irradiation is used.

The term "free from a carrier," as used herein, refers to the osteoinductive implant of the present disclosure not being disposed in a carrier (e.g., glycerol). Thus, the osteoinductive implant is more than 95% to 99.9% to 100% free from carriers including, but not limited to, carriers such as hydroxyethyl cellulose, hydroxypropyl cellulose, hydroxyethylmethyl cellulose, hydroxypropylmethyl cellulose, poly(alpha-hydroxy acids), poly(lactide-co-glycolide) (PLGA or PLG), polylactide (PLA), polyglycolide (PG), polyethylene glycol (PEG) conjugates of poly (alpha-hydroxy acids), polyorthoesters, polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D,L-lactide, or L-lactide, caprolactone, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate), glycerol or combinations thereof. This is before or during e-beam sterilization. In some embodiments, after e-beam sterilization, the osteoinductive implant can be hydrated to a putty or a paste before it is implanted.

The term "sterilization," as used herein, refers to exposing the bone fibers to a sterilizing beam of accelerated electrons, i.e., an electron beam (e-beam). The particle beam which comprises the e-beam can include directional bombardment, i.e., bombardment from one direction only, and can include single-side or multiple-side irradiation.

The term "bioburden," as used herein, refers to the number of bacteria living on a surface that has not been sterilized. "Bioburden reduction," as used herein, refers to the reduction of microorganisms on the surface of an implant. In some embodiments, the bioburden may be reduced from about 1-log to about 10-log reduction in CFUs when subjecting the implant to electron beam irradiation. In some embodiments, the log reduction of subjecting the implant to electron beam irradiation is a 1, 2, 3, 4, 5, 6, 7, 8, 9 or 10-log reduction.

The term "sterility assurance level" or "SAL," as used herein, refers to the probability of a single unit being non-sterile after it has been subjected to sterilization. In some embodiments, the SAL is about $10^{-1}$, about $10^{-1}$, about $10^{-4}$, about $10^{-3}$, about $10^{-2}$, or about $10^{-1}$.

The implant can have wicking properties as a result of the DBM fibers. The term "wicking" or a "wicking feature" as used herein, refers to the graft being able to absorb or draw off a liquid in narrow spaces without assistance via capillary action. The wicking may occur due to the surface characteristics of the demineralized bone fibers, and/or the arrangement or configuration of the demineralized bone fibers. In some embodiments, when the implant decreases in moisture content, the wicking capability increases. A wicking material can include demineralized bone fibers. Additional wicking materials may be synthetic and/or natural. In some embodiments, the wicking materials may be formed as a woven material, including a braid, a nonwoven matrix, axially aligned, or in any other suitable manner.

The term "moisture content" as used herein, refers to the amount or percentage of fluid present in the implant either before or after irradiation. In some embodiments, the implant comprises a moisture content of about 1, 2, 3, 4, 5, 6, 7, 8, 9, 10, 11, 12, 13, 14, 15, 16, 17, 18, 19 or 20%.

The term "patient" refers to a biological system to which a treatment can be administered. A biological system can include, for example, an individual cell, a set of cells (e.g., a cell culture), an organ, or a tissue. Additionally, the term "patient" can refer to animals, including, without limitation, humans.

The term "demineralized," as used herein, refers to any material generated by removing mineral material from tissue, e.g., bone tissue. In certain embodiments, the demineralized compositions described herein include preparations containing less than 5%, 4%, 3%, 2% or 1% calcium by weight. Partially demineralized bone (e.g., preparations with greater than 5% calcium by weight but containing less than 100% of the original starting amount of calcium) is also considered within the scope of the disclosure. In some embodiments, partially demineralized bone contains preparations with greater than 5%, 10%, 15%, 20%, 25%, 30%, 35%, 40%, 45%, 50%, 55%, 60%, 65%, 70%, 75%, 80%, 85%, 90%, 95%, 96%, 97%, 98% or 99% of the original starting amount of calcium. In some embodiments, demineralized bone has less than 95% of its original mineral content. In some embodiments, demineralized bone has less than 95%, 90%, 85%, 80%, 75%, 70%, 65%, 60%, 55%, 50%, 45%, 40%, 35%, 30%, 25%, 20%, 15%, 10%, or 5% of its original mineral content. Demineralized is intended to encompass such expressions as "substantially demineralized," "partially demineralized," and "fully demineralized." In some embodiments, part or all of the surface of the bone can be demineralized. For example, part or all of the surface of the allograft can be demineralized to a depth of from about 100 to about 5000 microns, or about 150 microns to about 1000 microns. In some embodiments, part or all of the surface of the allograft can be demineralized to a depth of from about 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3050, 3100, 3150, 3200, 3250, 3300, 3350, 3400, 3450, 3500, 3550, 3600, 3650, 3700, 3750, 3800, 3850, 3900, 3950, 4000, 4050, 4100, 4150, 4200, 4250, 4300, 4350, 4400, 4450, 4500, 4550, 4600, 4650, 4700, 4750, 4800, 4850, 4900, 4950 to about 5000 microns. If desired, the outer surface of the intervertebral implant can be masked with an acid resistant coating or otherwise treated to selectively demineralize unmasked portions of the outer surface of the intervertebral implant so that the surface demineralization is at discrete positions on the implant.

The term "demineralized bone matrix," as used herein, refers to any material generated by removing mineral material from bone tissue. In some embodiments, the DBM compositions as used herein include preparations containing less than 5%, 4%, 3%, 2% or 1% calcium by weight.

The term "superficially demineralized," as used herein, refers to bone-derived elements possessing at least about 90, 91, 92, 93, 94, 95, 96, 97, 98 or 99 weight percent of their original inorganic mineral content. The expression "partially demineralized" as used herein refers to bone-derived elements possessing from about 8 to about 90 weight percent of their original inorganic mineral content. In some embodiments, partially demineralized refers to bone-derived elements possessing from about 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88 to about 90 weight percent of their original inorganic mineral content. The expression "fully demineralized" as used herein refers to bone containing less than 8%, 7%, 6%, 5%, 4%, 3%, 2%, or 1% of its original mineral context.

The terms "pulverized bone", "powdered bone" or "bone powder" as used herein, refers to bone particles of a wide range of average particle size ranging from relatively fine powders to coarse grains and even larger chips.

The allograft can comprise bone fibers. Fibers include bone elements whose average length to average thickness ratio or aspect ratio of the fiber is from about 50:1 to about 1000:1. In overall appearance the fibrous bone elements can be described as elongated bone fibers, threads, narrow strips, or thin sheets. Often, where thin sheets are produced, their edges tend to curl up toward each other. The fibrous bone elements can be substantially linear in appearance or they can be coiled to resemble springs. In some embodiments, the elongated bone fibers are of irregular shapes including, for example, linear, serpentine or curved shapes. The elongated bone fibers are preferably demineralized, however, some of the original mineral content may be retained when desirable for a particular embodiment. The fibers when wet relax because they are porous, as they dry, they become more entangled and form a coherent mass as the fibers interconnect. In some embodiments, even when the fibers are wet, they are still cohesive.

"Non-fibrous", as used herein, refers to elements that have an average width substantially smaller than the average thickness of the fibrous bone element or aspect ratio of less than from about 50:1 to about 1000:1. For example, allograft bone fibers will have a fiber shape, while the non-fibrous material will not have a fiber shape but will have a shape such as, for example, triangular prism, sphere, cube, cylinder, square, triangle, particle, powder, and other regular or irregular shapes.

"Pressed bone fibers", as used herein, refer to bone fibers formed by applying pressure to bone stock. The bone utilized as the starting, or stock, material may range in size from relatively small pieces of bone to bone of such dimensions as to be recognizable as to its anatomical origin. The bone may be substantially fully demineralized, surface demineralized, partially demineralized, or nondemineralized. In general, the pieces or sections of whole bone stock can range from about 1 to about 400 mm, from about 5 to about 100 mm, in median length, from about 0.5 to about 20 mm, or from about 2 to about 10 mm, in median thickness and from about 1 to about 20 mm, or from about 2 to about 10 mm, in median width. Forming bone fibers by pressing results in intact bone fibers of longer length than other methods of producing the elongate bone fibers retaining more of the native collagen structure. The bone fibers may be made via a cartridge mill.

"High porosity", as used herein refers to having a pore structure that is conducive to cell ingrowth, and the ability to promote cell adhesion, proliferation and differentiation.

"Resorbable", as used herein, refers to a material that exhibits chemical dissolution when placed in a mammalian body.

"Bioactive agent" or "bioactive compound", as used herein, refers to a compound or entity that alters, inhibits, activates, or otherwise affects biological or chemical events. For example, bioactive agents may include, but are not limited to, osteogenic or chondrogenic proteins or peptides, anti-AIDS substances, anti-cancer substances, antibiotics, immunosuppressants, anti-viral substances, enzyme inhibitors, hormones, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-ECM interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, angiogenic factors, anti-secretory factors, anticoagulants and/or antithrombotic agents, local anesthetics, ophthalmics, prostaglandins, anti-depressants, anti-psychotic substances, anti-emetics, and imaging agents. In certain embodiments, the bioactive agent is a drug. In some embodiments, the bioactive agent is a growth factor, cytokine, ECM molecule or a fragment or derivative thereof, for example, a cell attachment sequence such as RGD.

"Coherent mass", as used herein, refers to a plurality of bone fibers, in some embodiments, bound to one another by mechanical interlocking properties of the fibers. The cohesive mass may be in a variety of shapes and sizes, and is implantable into a surgical location. The cohesive mass comprises at least two curled or partially curled bone fibers that entangle with one another to maintain a connection without the use of a binding agent or carrier. In some embodiments, the fibers when wet relax because they are porous, as they dry, they become more entangled and form a coherent mass as the fibers interconnect.

The term "oxysterol" as used herein is meant to encompass one or more forms of oxidized cholesterol. The oxysterols described herein are either independently or collectively active to bone growth in a patient, as described in WO 2013169399 A1, which is hereby incorporated by reference in its entirety.

The oxysterol can be in a pharmaceutically acceptable salt. Some examples of potentially pharmaceutically acceptable salts include those salt-forming acids and bases that do not substantially increase the toxicity of a compound, such as, salts of alkali metals such as magnesium, potassium and ammonium, salts of mineral acids such as hydrochloride, hydriodic, hydrobromic, phosphoric, metaphosphoric, nitric and sulfuric acids, as well as salts of organic acids such as tartaric, acetic, citric, malic, benzoic, glycollic, gluconic, gulonic, succinic, arylsulfonic, e.g., p-toluenesulfonic acids, or the like.

Pharmaceutically acceptable salts of oxysterol include salts prepared from pharmaceutically acceptable non-toxic bases or acids including inorganic or organic bases, inorganic or organic acids and fatty acids. Salts derived from inorganic bases include aluminum, ammonium, calcium, copper, ferric, ferrous, lithium, magnesium, manganic salts, manganous, potassium, sodium, zinc, and the like. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethyl amine, tripropylamine, tromethamine, and the like. When the compound of the current application is basic, salts may be prepared from pharmaceutically acceptable non-toxic acids, including inorganic and organic acids. Such acids include acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Fatty acid salts may also be used, e.g., fatty acid salts having greater than 2 carbons, greater than 8 carbons or greater than 16 carbons, such as butyric, caproic, caprylic, capric, lauric, mystiric, palmitic, stearic, arachidic or the like.

In some embodiments, in order to reduce the solubility of the oxysterol to assist in obtaining a controlled release depot effect, the oxysterol is utilized as the free base or utilized in a salt which has relatively lower solubility. For example, the present application can utilize an insoluble salt such as a fatty acid salt. Representative fatty acid salts include salts of oleic acid, linoleic acid, or fatty acid salts with between 8 to 20 carbons solubility, such as for example, palmeate or stearate.

The oxysterol can be "osteogenic," where it can enhance or accelerate the ingrowth of new bone tissue.

Reference will now be made in detail to certain embodiments of the disclosure. The disclosure is intended to cover all alternatives, modifications, and equivalents that may be included within the disclosure as defined by the appended claims.

The headings below are not meant to limit the disclosure in any way; embodiments under any one heading may be used in conjunction with embodiments under any other heading.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

Electron Beam Irradiation

A method of making an electron beam irradiated osteoinductive implant is provided. The method comprises exposing an osteoinductive implant containing demineralized bone matrix (DBM) fibers to electron beam radiation at a dose of from about 10 kilograys (kGy) to 100 kilograys for a period of time to reduce microorganisms in the osteoinductive implant and to obtain the electron beam irradiated osteoinductive implant, wherein the electron beam irradiated osteoinductive implant retains osteoinductive properties.

The implant is free from a carrier, and in some embodiments is glycerol free. The term "free from a carrier," as used herein, refers to the implant of the present disclosure not being administered, retained or disposed in a carrier. Carriers include but are not limited to polymeric carriers in solid or liquid form. In some embodiments, the implant is not free from a carrier and is added to a carrier after the implant has been irradiated by electron beam radiation, as described below.

In some embodiments, the DBM fibers of the implant are lyophilized or dried before exposing the DBM fibers to electron beam radiation. In some embodiments, the DBM fibers of the implant are lyophilized or dried after exposing the DBM fibers to electron beam radiation.

In some embodiments, the implant is hydrated after it has been electron beam irradiated to form a moldable or malleable putty or a paste, as described below.

In some embodiments, the implant is exposed to electron beam radiation at a dose of from about 10 kilograys (kGy) to about 100, about 10 kilograys to about 90 kilograys, about 10 kilograys to about 80 kilograys, about 10 kilograys to about 70 kilograys, about 10 kilograys to about 60 kilograys, about 10 kilograys to about 50 kilograys, about 10 kilograys to about 40 kilograys, about 10 kilograys to about 30 kilograys, about 10 kilograys to about 20 kilograys, about 15 to about 100 kilograys, about 15 to about 90 kilograys, about 15 kilograys to about 80 kilograys, about 15 kilograys to about 70 kilograys, about 15 kilograys to about 60 kilograys, about 15 kilograys to about 50 kilograys, about 15 to about 40 kilograys, about 15 kilograys to about 30 kilograys, about 15 kilograys to about 20 kilograys, about 20 kilograys to about 100 kilograys, about 20 kilograys to about 90 kilograys, about 20 kilograys to about 80 kilograys, about 20 kilograys to about 70 kilograys, about 20 kilograys to about 60 kilograys, about 20 kilograys to about 50 kilograys, about 20 kilograys to about 40 kilograys, about 20 kilograys to about 30 kilograys, and/or about 20 kilograys to about 25 kilograys.

In some embodiments, the implant is exposed to electron beam radiation at a dose of about 10, 15, 20, 25, 30, 35, 40, 45, 50, 55, 60, 65, 70, 75, 80, 85, 90, 95, and/or 100 kilograys.

In some embodiments, the implant is exposed to a dose or a plurality of doses of electron beam radiation. In some embodiments, the implant is exposed to a plurality of the same or different doses of the electron beam radiation. In some embodiments, the implant is exposed to 1, 2, 3, 4, 5, 6, 7, 8, 9 or 10 doses of electron beam radiation. In some embodiments, the dose is uniform or is a non uniform dose. In some embodiments, the electron beam radiation irradiates all or only a portion of the implant.

The implant is exposed to electron beam radiation at a temperature of about 15° C. to about 27° C., about 18° C. to about 24° C., about 19° C. to about 23° C., or about 20° C. to about 21° C. In some embodiments, the implant is exposed to electron beam radiation at a temperature of about 15, 16, 17, 18, 19, 20, 21, 22, 23, 24, 25, 26 or about 27° C.

The implant is exposed to electron beam radiation for a period of time from about 1 minute to about 60 minutes, from about 1 minute to about 45 minutes, from about 1 minute to about 30 minutes, from about 1 minute to about 15 minutes, from about 1 minute to about 10 minutes, from about 1 minute to about 5 minutes, from about 1 minute to about 4 minutes, from about 1 minute to about 3 minutes, or from about 1 minute to about 2 minutes. In some embodiments, the implant is exposed to electron beam irradiation for a period of time at about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or about 60 minutes.

The implant is exposed to electron beam radiation at an energy range from about 80 to about 300 keV, 300 keV to about 5 MeV, or above 5 MeV.

In some embodiments, exposing the implant to electron beam radiation reduces microorganisms to a sterility assurance level (SAL) of about $10'$. In some embodiments, the SAL is about $10^{-6}$, about $10^{-5}$, about $10^{-4}$, about $10^{3}$, about $10^{-2}$, or about $10^{-1}$.

In some embodiments, exposing the implant to electron beam radiation reduces microorganisms by a 1-log to a 10-log reduction, a 1-log to a 9-log reduction, a 1-log to an 8-log reduction, a 1-log to a 7-log reduction, a 1-log to a 6-log reduction, a 1-log to a 5-log reduction, a 1-log to a 4-log reduction, a 1-log to a 3-log reduction, or a 1-log to a 2-log reduction. In some embodiments, exposing the implant to electron beam irradiation reduces microorganisms by a 1, 2, 3, 4, 5, 6, 7, 8, 9 or 10-log reduction.

In some embodiments, exposing the implant to electron beam radiation sterilizes the implant such that the implant is from about 90 to about 99.9% sterile. In some embodiments, the implant is about 90, 91, 92, 93, 94, 95, 96, 97, 98, 99 or 99.9% sterile.

In some embodiments, microorganisms include but are not limited to viruses, bacteria, pyrogens, prions, microorganisms and/or pathogens. In some embodiments, some bacteria which may be treated include, but are not limited to the following: *Staphylococcus; Streptococcus*, including *S. pyogenes; Enterococci; Bacillus*, including *Bacillus anthracis*, and *Lactobacillus; Listeria; Corynebacterium diphtheriae; Gardnerella* including *G. vaginalis; Nocardia; Streptomyces; Thermoactinomyces vulgaris; Treponema; Camplyobacter; Pseudomonas* including *P. aeruginosa; Legionella; Neisseria* including *N. gonorrhoeae* and *N. meningitides; Flavobacterium* including *F. meningosepticum* and *F. odoratum; Brucella; Bordetella* including *B. pertussis* and *B. bronchiseptica; Escherichia* including *E. coli; Klebsiella; Enterobacter; Serratia* including *S. marcescens* and *S. liquefaciens; Edwardsiella; Proteus* including *P. mirabilis* and *P. vulgaris; Streptobacillus*; Rickettsiaceae including *R. rickettsii; Chlamydia* including *C. psittaci* and *C. trachomatis; Mycobacterium* including *M. tuberculosis, M. intracellulare, M. fortuitum, M. laprae, M. avium, M. bovis, M. africanum, M. kansasii, M. intracellulare*, and *M. lepraemurium*; and *Nocardia*, and any other bacteria containing lipid in their membranes.

In some embodiments, electron beam irradiating the implant can remove infectious agents including, viruses, bacteria, mycobacteria, mycoplasma, fungi, prions and/or constituents thereof. In various embodiments, methods of this application are applicable to removing viruses of the family of Togaviridae, in particular of the genus Alphavirus, such as the Hepatitis C virus, and for preventing their transmission during tissue grafts; for combating viruses of the family Picorviridae, in particular of the genus Enterovirus, more particularly the Polio Sabin virus, and preventing their transmission during tissue grafts; for combating viruses of the family Herpesviridae and preventing their transmission during tissue grafts; for combating viruses of the family Retroviridae, in particular of the genus Lentivirus, more particularly human HIV immunodeficiency viruses, and preventing their transmission during tissue grafts.

In some embodiments, electron beam irradiating the implant inactivates viruses, especially enveloped or lipid-coated viruses, and nonenveloped, protein encased viruses in proteinaceous products without incurring substantial denaturation. In various embodiments, electron beam irradiating the implant inactivates virus and virus-like particles.

In some embodiments, viral infectious organisms which may be inactivated by electron beam irradiating the implant include, but are not limited to, the lipid-containing viruses of the following genuses: Alphavirus (alphaviruses), Rubivurus (rubella virus), Flavivirus (Flaviviruses), Pestivirus (mucosal disease viruses), (unnamed, hepatitis C virus), Coronavirus, (Coronaviruses), Torovirus, (toroviruses), Arteivirus, (arteriviruses), Paramyxovirus, (Paramyxoviruses), Rubulavirus (rubulavriuses), Morbillivirus (morbillivuruses), Pneumovirinae (the pneumoviruses), Pneumovirus (pneumoviruses), Vesiculovirus (vesiculoviruses), Lyssavirus (lyssaviruses), Ephemerovirus (ephemeroviruses), Cytorhabdovirus (plant rhabdovirus group A), Nucleorhabdovirus (plant rhabdovirus group B), Filovirus (filoviruses), Influenzavirus A, B (influenza A and B viruses), Influenza virus C (influenza C virus), (unnamed, Thogoto-like viruses), Bunyavirus (bunyaviruses), Phlebovirus (phleboviruses), Nairovirus (nairoviruses), Hantavirus (hantaviruses), Tospovirus (tospoviruses), Arenavirus (arenaviruses), unnamed mammalian type B retroviruses, unnamed, mammalian and reptilian type C retroviruses, unnamed type D retroviruses, Lentivirus (lentiviruses), Spumavirus (spumaviruses), Orthohepadnavirus (hepadnaviruses of mammals), Avihepadnavirus (hepadnaviruses of birds), Simplexvirus (simplexviruses), Varicellovirus (varicelloviruses), Betaherpesvirinae (the cytomegaloviruses), Cytomegalovirus (cytomegaloviruses), Muromegalovirus (murine cytomegaloviruses), Roseolovirus (human herpes virus 6), Gammaherpesvirinae (the lymphocyte-associated herpes viruses), Lymphocryptovirus (Epstein-Bar-like viruses), Rhadinovirus (saimiri-ateles-like herpes viruses), Orthopoxvirus (orthopoxviruses), Parapoxvirus (parapoxviruses), Avipoxvirus (fowlpox viruses), Capripoxvirus (sheeppoxlike viruses), Leporipoxvirus (myxomaviruses), Suipoxvirus (swine-pox viruses), Molluscipoxvirus (molluscum contagiosum viruses), Yatapoxvirus (yabapox and tanapox viruses), Unnamed, African swine fever-like viruses, Iridovirus (small iridescent insect viruses), Ranavirus (front iridoviruses), Lymphocystivirus (lymphocystis viruses of fish), Togaviridae, Flaviviridae, Coronaviridae, Enabdoviridae, Filoviridae, Paramyxoviridae, Orthomyxoviridae, Bunyaviridae, Arenaviridae, Retroviridae, Hepadnaviridae, Herpesviridae, Poxyiridae, and any other lipid-containing virus.

In various embodiments, these viruses include the following human and animal pathogens: Ross River virus, fever virus, dengue viruses, Murray Valley encephalitis virus, tick-borne encephalitis viruses (including European and far eastern tick-borne encephalitis viruses), human coronaviruses 229-E and OC43 and others (causing the common cold, upper respiratory tract infection, probably pneumonia and possibly gastroenteritis), human parainfluenza viruses 1 and 3, mumps virus, human parainfluenza viruses 2, 4a and 4b, measles virus, human respiratory syncytial virus, rabies virus, Marburg virus, Ebola virus, influenza A viruses and influenza B viruses, Arenaviruss: lymphocytic choriomeningitis (LCM) virus; Lassa virus, human immunodeficiency viruses 1 and 2, or any other immunodeficiency virus, hepatitis A virus, hepatitis B virus, hepatitis C virus, Subfamily: human herpes viruses 1 and 2, herpes virus B, Epstein-Barr virus), (smallpox) virus, cowpox virus, molluscum contagiosum virus.

All protozoa containing lipid, especially in their plasma membranes, are included within the scope of the present application. In some embodiments, protozoa that may be inactivated by electron beam irradiating the implant include, but are not limited to, the following lipid-containing protozoa: *Trypanosoma brucei, Trypanosoma gambiense, Trypanosoma cruzi, Leishmania donovani, Leishmania vianni, Leishmania tropica, Giardia lamblia, Giardia intestinalis; Trichomonas vaginalis, Entamoeba histolytica, Entamoeba coli, Entamoeba hartmanni, Naegleria* species, *Acanthamoeba* species, *Plasmodium falciparum, Plasmodium vivax, Plasmodium malariae, Plasmodium ovale, Toxoplasma gondii, Cryptosporidium parvum, Cryptosporidium muris, Isospora belli, Cyclospora cayetansis, Balantidium* species, *Babesia bovis, Babesia, microti, Babesia divergens, Encephalitozoon intestinalis, Pleistophora* species, *Nosema ocularum, Vittaforma corneae, Septata intestinalis, Enterocytozoon, Dientamoeba fragilis, Blastocystis* species, *Sarcocystis* species, *Pneumocystis carinii, Microsporidium africanum, Microsporidium ceylonensis, Eimeria acervulina, Eimeria maxima, Eimeria tenella* and *Neospora caninum*. It is to be understood that the present application is not limited to the protozoa provided in the list above.

In some embodiments, electron beam irradiating the implant can treat protozoa including Coccidia, which includes *Isospora* species, *Cryptosporidium* species, *Cyclospora* species, *Toxoplasma* species, *Sarcocystis* species, *Neospora* species, and *Eimeria* species. These coccidian parasites cause intestinal disease, lymphadenopathy, encephalitis, myocarditis, and pneumonitis.

The terms "protozoal infection" or "infectious disease" mean diseases caused by protozoal infectious organisms. The diseases include, but are not limited to, African sleeping sickness, Chagas' disease, Leishmaniasis, Giardiasis, Trichomoniasis, amebiasis, primary amebic encephalitis, granulomatous amebic encephalitis, malaria, Toxoplasmosis, Cryptosporidiosis, Isosporiasis, Cyclosporiasis, Balantidiasis, Babesiosis, microsporidiosis, *Dientamoeba fragilis* infection, *Blastocystis hominis* infection, Sarcosporidiosis, pneumonia, and coccidiosis. In some embodiments, protozoal infection treated with the method of the present application is Coccidiosis, which is caused by *Isospora* species, *Cryptosporidium* species, *Cyclospora* species, *Toxoplasma* species, *Sarcocystis* species, *Neospora* species, and *Eimeria* species. These coccidian parasites cause human intestinal disease, lymphadenopathy, encephalitis, myocarditis, and pneumonitis. These coccidian parasites also cause disease in animals, including cattle, dogs, cats, and birds. Avians, and chickens, turkeys and quail in particular, are affected by Coccidiosis, especially by *Eimeria* species such as *E. acervulina, E. maxima, E. necatrix, E. bruneti, E. mitis, E. praecox* and *E. tenella*.

In some embodiments, exposing the implant to electron beam radiation reduces the implants osteoinductivity score. In some embodiments, the implant's osteoinductivity score is reduced from a 4 to a 3. In some embodiments, the implant's osteoinductivity score stays the same at a 4, however, the percentage of osteoinductivity is slightly decreased.

In some embodiments, the electron beam irradiated osteoinductive implant retains its osteoinductive properties. In various embodiments, exposing the implant to electron beam radiation decreases the osteoinductive properties of the irradiated osteoinductive implant only by up to 20, 19, 18, 17, 16, 15, 14, 13, 12, 11, 10, 9, 8, 7, 6, 5, 4, 3, 2, 1 or 0%. In some embodiments, exposing the implant to electron beam radiation decreases the osteoinductive properties of the irradiated osteoinductive implant by only 0 to up to 2%, by 0 to up to 3%, by 0 to up to 4%, by 0 to up to 5%, by 0 to up to 6%, by 0 to up to 7%, by 0 to up to 8%, by 0 to up to 9%, by 0 to up to 10%, by 0 to up to 11%, by 0 to up to 12%, by 0 to up to 13%, by 0 to up to 14%, by 0 to up to 15%, by 0 to up to 16%, by 0 to up to 17%, by 0 to up to 18%, by 0 to up to 19%, or by 0 to up to 20%.

A method of treating a bone cavity is provided. The method comprising: implanting an osteoinductive implant into the bone cavity, the osteoinductive implant being irradiated with electron beam radiation at a dose of from about 10 kilograys to 100 kilograys for a period of time to reduce microorganisms in the osteoinductive implant, the osteoinductive implant containing demineralized bone matrix (DBM) fibers and being free of a carrier.

In some embodiments, the implant is glycerol free. In various embodiments, the method further comprises hydrating the osteoinductive implant with a liquid before implanting. In some embodiments, after hydrating, the osteoinductive implant forms into a putty or paste. In some embodiments, the method further comprises molding the osteoinductive implant into a shape after hydrating but before implanting.

In some embodiments, exposing the implant containing demineralized bone matrix fibers to the electron beam radiation reduces microorganisms to a sterility assurance level (SAL) of about $10^{-6}$. In some embodiments, the SAL is about $10^{-6}$, about $10^{-5}$, about $10^{-4}$, about $10^{-3}$, about $10^{-2}$, or about $10^{-1}$.

In some embodiments, exposing the implant to electron beam radiation reduces microorganisms by a 1-log to a 10-log reduction, a 1-log to a 9-log reduction, a 1-log to an 8-log reduction, a 1-log to a 7-log reduction, a 1-log to a 6-log reduction, a 1-log to a 5-log reduction, a 1-log to a 4-log reduction, a 1-log to a 3-log reduction, or a 1-log to a 2-log reduction. In some embodiments, exposing the implant to electron beam radiation reduces microorganisms by a 1, 2, 3, 4, 5, 6, 7, 8, 9 or 10-log reduction.

In some embodiments, before the implant is electron beam irradiated, it is disposed/placed in a container. The implant is then irradiated in the container. In some embodiments, the containers should be air tight (gas impermeable) and liquid tight, and withstand a wide temperature range so that the container is not damaged during irradiation or storage. In some embodiments, the container comprises a foil, a wrapping, an opaque pouch, a transparent pouch, or a glass container. The container walls can be formed from a suitable material, such as polyethylene terephthalate, polyethylene vinyl alcohol and aluminum foil, or multi-layered compositions, such as polyethylene vinyl alcohol and polypropylene compositions. In some embodiments, the container can be of various thicknesses and dimensions. In some embodiments, the container can be about 1 mm thick to about 10 cm thick. In some embodiments, the container can be about 1 mm to about 9 cm, about 1 mm to about 8 cm thick, about 1 mm to about 7 cm, about 1 mm to about 6 cm, about 1 mm to about 5 cm, about 1 mm to about 4 cm, about 1 mm to about 3 cm, or about 1 mm to about 2 cm, or about 1 mm to about 1 cm thick. In some embodiments, the implant is placed/disposed in a container after it has been irradiated.

Osteoinductive Implant

In some embodiments, an osteoinductive implant is provided. The osteoinductive implant comprises demineralized bone matrix (DBM) fibers that are free from a carrier. The osteoinductive implant is irradiated with electron beam radiation at a dose of from about 10 kilograys to 100 kilograys for a period of time to reduce microorganisms in the osteoinductive implant. The osteoinductive properties of the irradiated osteoinductive implant decreases only from about $0^{0}$c to 20%. In some embodiments, osteoinductive properties of the irradiated osteoinductive implant decreases only from about 0, 1, 2, 3, 4, 5, 6, 7, 8, 9, 10, 11, 12, 13, 14, 15, 16, 17, 18, 19 to 20%. In various embodiments, the osteoinductive properties of the irradiated osteoinductive implant is measured up to 6, 12, 18, 24, 32 or 36 months after storage at room temperature in a moisture barrier packaging.

In some embodiments, the implant is not free from a carrier and is added to a carrier after the implant has been irradiated by electron beam radiation. Suitable carriers include but are not limited to liquid and/or solid carriers. In some embodiments, the carrier comprises biopolymers and synthetic polymers such as human skin, human hair, bone, collagen, fat, thin cross-linked sheets containing fibers and/or fibers and chips, polyethylene glycol (PEG), chitosan, alginate sheets, cellulose sheets, hyaluronic acid sheet, as well as copolymer blends of poly (lactide-co-glycolide) PLGA.

In some embodiments, the carrier can also include other biocompatible and bioresorbable substances. The carrier may include, for example, natural polymers such as proteins and polypeptides, glycosaminoglycans, proteoglycans, elastin, hyaluronic acid, dermatan sulfate, gelatin, or mixtures or composites thereof. Synthetic polymers may also be incorporated into the carrier. These include, for example biodegradable synthetic polymers such as polylactic acid, polyglycolide, polylactic polyglycolic acid copolymers ("PLGA"), polycaprolactone ("PCL"), poly(dioxanone), poly(trimethylene carbonate) copolymers, polyglyconate, poly(propylene fumarate), poly(ethylene terephthalate), poly(butylene terephthalate), polyethylene glycol, polycaprolactone copolymers, polyhydroxybutyrate, polyhydroxyvalerate, tyrosine-derived polycarbonates and any random or (multi-)block copolymers, such as bipolymer, terpolymer, quaterpolymer, etc., that can be polymerized from the monomers related to previously-listed homo- and copolymers.

In some embodiments, the bioerodible polymer may have a molecular weight of from about 1,000 to about 30,000 Daltons (Da). In various embodiments, the polymer may have a molecular weight of from about 2,000 to about 10,000 Da. In some embodiments, the polymer may have a molecular weight of from about 2,000 to 4,000 Da or from about 3,000 to 4,000 Da. In some embodiments, the bioerodible polymer may have a molecular weight of 1,000, 2,000, 3,000, 4,000, 5,000, 6,000, 7,000, 8,000, 9,000, 10,000, 11,000, 12,000, 13,000, 14,000, 15,000, 16,000, 17,000, 18,000, 19,000, 20,000, 21,000, 22,000, 23,000, 24,000, 25,000, 26,000, 27,000, 28,000, 29,000 or about 30,000 Da.

In some embodiments, the implant is provided without a carrier and contains DBM fibers processed in such a way that it provides for cohesion between fibers without additional containment or binding agents to be provided. Bone shafts are milled to create curled bone fibers which are subsequently demineralized and freeze-dried. The fiber shape is altered during the drying process, which leads to physical entanglement and surface to surface interactions between adjacent fibers. The entanglement/interaction of the fibers is responsible for the cohesiveness of the final product.

Thus, the present disclosure provides for a fibrous bone material having a size and shape that provides for increased surface area and the ability to mechanically interlock with one another to form an implant.

In some embodiments, the DBM fibers are human bone fibers and comprise a length from about 1 to about 70 micrometers, from about 125 to about 250 micrometers, from about 10 micrometers to about 500 micrometers or from about 250 to about 500 micrometers. In some embodiments, the DBM fibers comprise have a length of about 1, 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, and/or 500 micrometers. In some embodiments, the fibers include a length from about 100 micrometers to about 2 mm. In some embodiments, the bone fibers have a length from about 0.5 cm to about 10 cm, about 1 cm to about 8 cm, about 3 cm to about 5 cm, about 0.5 mm to about 50 mm, about 1.0 mm to about 25 mm, or about 5 mm to about 10 mm. The fibers include a diameter of about 100 micrometers to about 2 mm.

In some embodiments, the fibers are milled in such a way as to provide increased surface area in a compact shape and size. In some embodiments, the fibers include a curled shape such that diameter of the curled fibers is between about 50 micrometers and about 3 mm, and the diameter of the fibers in a flattened configuration is about 125 micrometers to about 5 mm. In some embodiments, the fibers include a curled shape such that diameter of the curled fibers is between about 100 micrometers and about 1 mm, and the diameter of the fibers in a flattened configuration is about 250 micrometers to about 2 mm.

In some embodiments, the fibers have a diameter from about 100 µm to about 2 mm. In some embodiments, the bone fibers have a length from about 0.5 mm to about 50 mm. In some embodiments, the bone fibers have an average length from about 0.5 cm to about 10 cm. In some embodiments, the fibers have an aspect ratio of from about 50:1 to about 1000:1, from about 50:1 to about 950:1, from about 50:1 to about 750:1, from about 50:1 to about 500:1, from about 50:1 to about 250:1, from about 50:1 to about 100:1, from about 10:1 to about 50:1, or from about 5:1 to about 10:1.

In some embodiments, the implant is glycerol free. In some embodiments, before the implant is hydrated, the implant comprises a low moisture content of less than 20%, 19%, 18%, 17%, 16%, 15%, 14%, 13%, 12%, 11%, 10%, 9%, 8%, 7%, 6%, 5%, 4%, 3%, 2%, or 1% moisture.

In some embodiments, the implant is hydrated after it has been electron beam irradiated to form a moldable or malleable putty or a paste. Once hydrated, the implant is placed into a surgical site at a location determined by a medical practitioner. The fibers in the implant maintain their coherency and mechanical interactions such that the putty requires no binding agent or carrier when placed in situ. In some embodiments, the implant is hydrated with a liquid before or after implantation of up to about 1% to about 60%. In some embodiments, the implant is hydrated with a liquid at about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 to about 60%.

In some embodiments, the liquid for hydrating the implant comprises blood, water, saline or a combination thereof. In some embodiments, the liquid for hydrating the implant is mixed with lyophilized fibers without a binder to form moldable lyophilized DBM fibers.

In some embodiments, the implant comprises a wicking feature configured to absorb a plurality of fluids. In some embodiments, the implant comprises a wicking feature configured to absorb a liquid for hydrating the implant. In some embodiments, when the implant decreases in moisture content, its wicking capability increases. A wicking material can include the DBM fibers. In some embodiments, additional wicking materials may be synthetic and/or natural. In some embodiments, the wicking materials may be formed as a woven material, including a braid, a nonwoven matrix, axially aligned, or in any other suitable manner.

In some embodiments, DBM compositions of the implant of the present disclosure allow osteogenesis, osteoinduction and/or osteoconduction. In some embodiments, the DBM compositions of the implant (e.g., bone fiber) are made from bone material that does not contain a binder.

In some embodiments, the bone material (e.g., DBM fibers) is lyophilized. In some embodiments, the DBM fibers are cartridge milled and have a ribbon-like shape and increased surface area. In some embodiments, a coherent mass of milled and lyophilized DBM fibers are cartridge milled fibers having a ribbon-like shape, increased surface area and a curled portion. In some embodiments, the coherent mass of milled and lyophilized DBM fibers comprises autograft or allograft bone.

In some embodiments, the bone material (e.g., DBM fibers) comprises cortical bone, cancellous bone, corticocancellous bone, or mixtures thereof. In some embodiments, the bone material is obtained from autogenous bone, allogenic bone, xenogenic bone, or mixtures thereof. In some embodiments, the implant comprising the DBM fibers is lyophilized and shaped. In some embodiments, the shape of the implant is cube, square, triangle, rectangular, circular, disc or cylinder shape.

In some embodiments, the implant is a bone graft material that is resorbed/remodeled and replaced by host bone during the healing process. In some embodiments, the bone material disclosed herein includes additional additives, such as synthetic ceramics and/or bioerodible polymers, which produce high concentrations of calcium, phosphate and silicon ions that act as a nidus for de-novo bone formation, as discussed herein. As the bioerodible polymer degrades faster than the ceramic, more and more osteoinductive DBM particles are exposed. The slower resorbing ceramic may act as a solid surface for stem cells and osteoblasts to attach to and begin laying down new bone.

The implant disclosed has good flexibility and is compression resistant. It is also osteoinductive with the demineralized bone matrix retaining activity. These properties make an excellent bone graft substitute in that it may not break, crack, or deform when implanted in the body.

The implant may be a combination of fibers of bone matrix from allograft bone and fibers of non-allograft bone material. The fibers of the non-allograft bone material comprise non-fibrous DBM particles embedded within or dispersed on the fibers of the non-allograft bone material. The ratio of fibers of DBM from allograft material to fibers of non-allograft material ranges from about 20:80 to about 70:30. In one embodiment, the ratio of fibers from allograft material to fibers of non-allograft material ranges from about 40:60 to about 60:40. In one embodiment, the ratio of fibers of DBM from allograft material to fibers of non-allograft material is about 50:50.

In some embodiments, the DBM includes particles that are non-fibrous. In some embodiments, the particles are powders, microspheres, sponges, pastes, gels, and/or granules. In one embodiment, the particles are powders.

In various embodiments, the fibers have an aspect ratio of length to width from about 50:1 to about 1000:1, from about 50:1 to about 950:1, from about 50:1 to about 750:1, from about 50:1 to about 500:1, from about 50:1 to about 250:1, from about 50:1 to about 100:1, from about 10:1 to about 50:1, or from about 5:1 to about 10:1. In other embodiments, the fibers have an aspect ratio of length to width of about 4:1, 17:1, or 23:1.

The composition has very low immunogenicity and good compatibility.

DBM fibers for use in the present disclosure can be obtained commercially or can be prepared by known techniques. In general, advantageous, osteoinductive DBM materials can be prepared by decalcification of cortical and/or cancellous bone fibers, often by acid extraction. The fibers can be milled for example cartridge milled. The acid extraction process can be conducted so as to leave collagen, noncollagenous proteins, and growth factors together in a solid fiber. Methods for preparing bioactive demineralized bone are described in U.S. Pat. Nos. 5,073,373; 5,484,601; and 5,284,655, as examples. DBM products are also available commercially, including for instance, from sources such as Regeneration Technologies, Inc. (Alachua, Fla.), The American Red Cross (Arlington, Va.), and others. Bone fibers that are solely osteoconductive can be prepared using similar techniques that have been modified or supplemented to remove or inactivate (e.g. by crosslinking or otherwise denaturing) components in the bone matrix responsible for osteoinductivity. Osteoinductive and/or osteoconductive DBM materials used in the present disclosure can be derived from human donor tissue, especially in regard to implant devices intended for use in human subjects.

In regard to the fiber content of the implant on a dry weight basis, the bone fiber material can constitute from about 5% to about 100% of the compositions, about 20% to about 80%, or about 25% to about 75% by weight.

In some embodiments, the bone fibers have an average length to average thickness ratio or aspect ratio of the fibers from about 50:1 to about 1000:1. In overall appearance the bone fibers can be in the form of ribbons, threads, narrow strips, and/or thin sheets. The elongated bone fibers can be substantially linear in appearance or they can be coiled to resemble springs. In some embodiments, the bone fibers have linear portions and coiled portions. In some embodiments, the bone fibers are of irregular shapes including, for example, linear, serpentine and/or curved shapes. In some embodiments, the fibers can be curled at the edges to have a substantially hemicircular cross-sections. In some embodiments, the fibers may be entirely or partially helical, circumvoluted or in the shape of a corkscrew. The elongated bone fibers can be demineralized however some of the original mineral content may be retained when desirable for a particular embodiment. The bone graft fiber may further comprise mineralized bone material.

Figure 3:
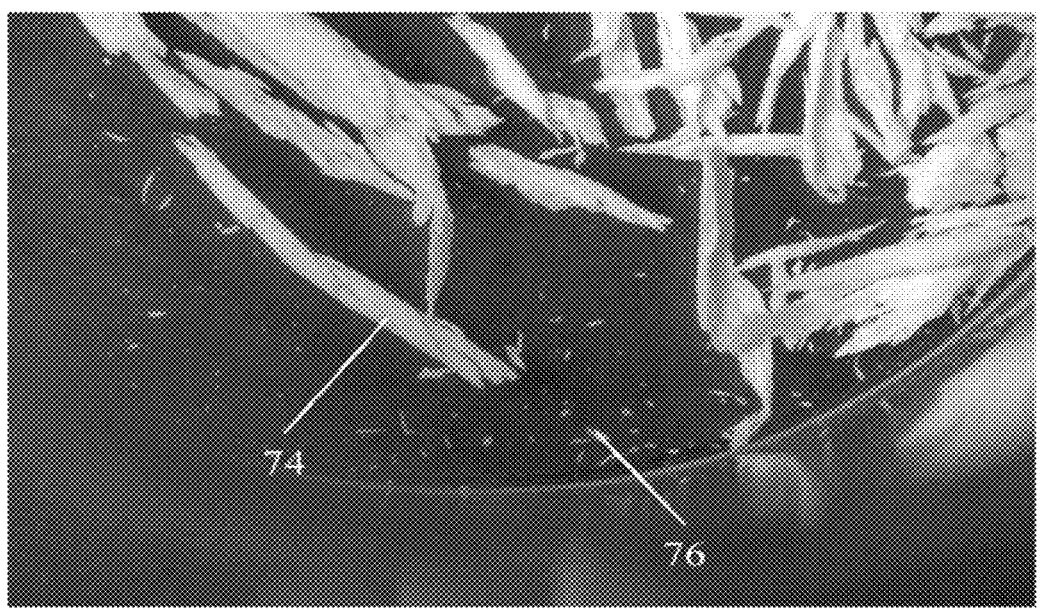
FIG. 3 depicts mineralized fibers having increased surface area. The fibers are milled from bone shafts using any appropriate apparatus, such as a cartridge mill. The fibers are milled to include curled shapes having frayed portions and/or hooked portions to facilitate mechanical interlocking of the fibers.
Figure 4:
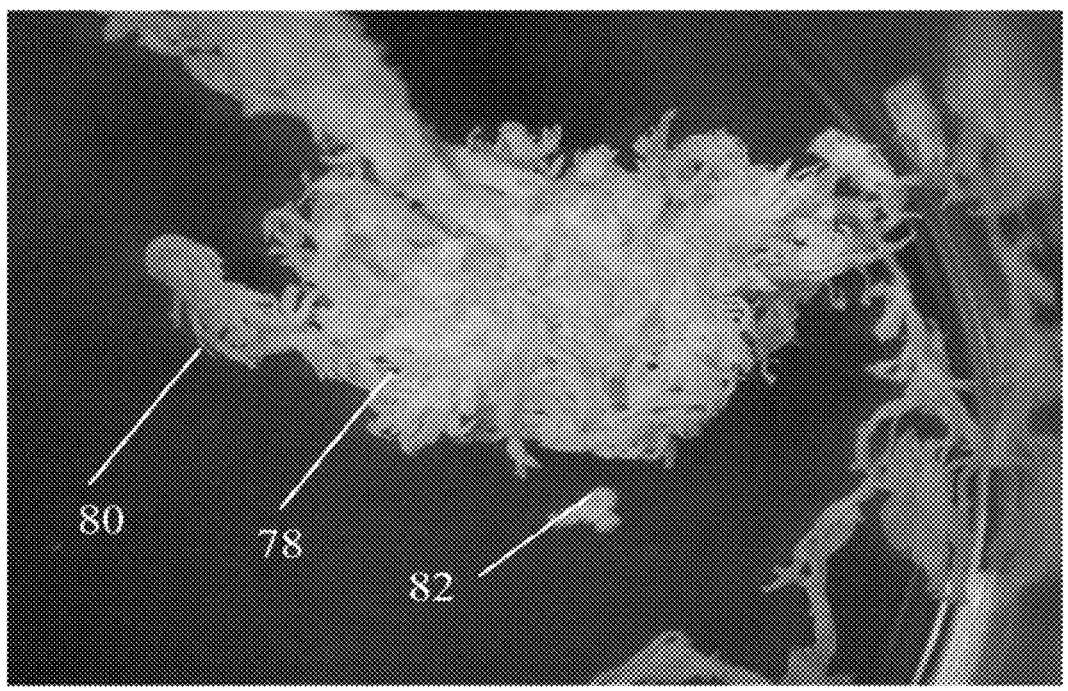
FIG. 4 depicts a bone material comprising a coherent mass of milled and lyophilized demineralized bone fibers. Lyophilization of the fibers alters the curls of the fibers to facilitate mechanical interlocking of the fibers. The lyophilized fibers form a coherent mass without the use of a binding agent or a carrier.

The bone fibers are elongated and curled to increase the surface area of the strips. The curled fibers may include frayed portions along the edges to facilitate interactions with other bone fibers. In some embodiments, the curled fibers are milled to have hooked portions along the edges of the fibers configured to engage with other fibers. Such frayed and hooked portions are illustrated, for example, in FIGS. 3 and 4. The hooked portions may engage other hooked portions, frayed portions, straightened portions or curled portions of other fibers. The hooked and frayed portions and the curled shape of the fibers provide for entanglement between fibers such that the fibers form a coherent mass without the need for a carrier or binding agent. For example, FIG. 3 illustrates bone fibers 74 produced from a cartridge mill. FIG. 4 illustrates a coherent mass of demineralized bone after it has been demineralized and contaminants remove by alcohol soaking, the wet fibers relax and entangle further after drying.

The bone fiber sizes and shapes may be created in a number of ways, for example, through cartridge milling. One such example of a suitable cartridge mill is the Osteobiologic Milling Machine, as described in U.S. Patent Publication No. 2012/0160945, assigned to Warsaw Orthopedic, Inc. and is hereby incorporated by reference in its entirety. However, it is contemplated that the bone fibers may be alternatively milled using vices, cutters, rollers, rotating rasps or reciprocating blade mills.

Non-Bone Material Additives

In some embodiments, after the implant comprising DBM fibers is formed, an active agent may be added to it before implantation. In some embodiments, the implant comprises an active agent comprising an oxysterol.

Oxysterols are a family of molecules consisting of oxygenated derivatives of cholesterol. Oxysterols are involved in many biological processes, and have been found to possess osteogenic properties. For example, one naturally occurring oxysterol, 20(S)-hydroxycholesterol, has osteogenic and anti-adipogenic properties. Such oxysterols can be useful in healing bone fractures, long bone fusion procedures, spinal fusion procedures, interbody spinal fusion procedures, posterolateral spinal fusion procedures, cervical discectomy and fusion procedures, dental procedures, and cranial/maxillofacial procedures.

Oxysterols also play a role in various physiological processes, such as cellular differentiation, inflammation, apoptosis, and steroid production. Oxysterols are products of cholesterol oxidation and are formed in vivo by a variety of cell types including osteoblasts (Schroepfer. *Phyiol Rev* 80:361-554, 2000; Bjorkhem and Dicsfalusy. *Arterioscler Thromb Vase Biol* 22:734-742, 2002). Certain oxysterols, such as 20(S)-hydroxycholesterol, as well as 22(S)- or 22(R)-hydroxycholesterol, induce osteogenic differentiation in multipotent mesenchymal cells such as M2-10B4 (M2) marrow stromal cells and C3H10T1/2 embryonic fibroblasts (Kha et al. *J Bone Miner Res* 19:830-840, 2004). Oxysterols can induce osteogenic and inhibit adipogenic differentiation of mesenchymal stem cells through activation of the hedgehog signaling pathway, which in turn regulates the master switches that control osteogenic and adipogenic differentiation, namely Runx2 and PPARγ, respectively (Richardson et al. *J Cell Biochem* 100:1131-1145, 2007; Dwyer et al. J Biol Chem 282: 8959-8968, 2007; Kim et al., *J Bone Miner Res* 22:1711-1719, 2007). Some oxysterols also provide therapeutic uses for treatment of bone defects or disorders such as osteoporosis.

In some embodiments, the implant comprises an oxysterol for induction of local bone formation and treatment of bone defects. The oxysterol is retained in the implant and is released over time, while the implant allows influx of bone cells to grow bone and fill the defect. In some embodiments, such applications are based on the ability of these oxysterol compounds to induce the hedgehog signaling pathway. In some embodiments, the implant causes mesenchymal stem cells to show induced expression of markers of osteoblast differentiation. The implant described herein can be used for a variety of therapeutic uses including but not limited to induction of local bone formation and treatment of bone defects. In some embodiments, implants containing oxysterol as described herein induce a biological response when the implant contacts a human or animal cell. In some embodiments, the cell can be a mesenchymal stem cell or a bone marrow stromal cell. In some embodiments, the biological response comprises stimulating osteoblastic differentiation, inhibiting adipocyte differentiation, or stimulating cartilage formation. In some embodiments, the implant is configured as an implant to release the oxysterol to induce a biological response at or near a surgical site or a bone defect site.

Oxysterols can be used to induce systemic bone formation to treat bone defects such as osteoporosis, to induce local bone formation to treat conditions such as nonunion fractures, or other bone disorders, such as jaw bone defects in dental applications/implants, and to induce spinal fusion. In some embodiments, the implant may include an oxysterol alone or in combination with one or more bone morphogenetic proteins or osteogenic agents. In some embodiments, more than one oxysterol is present in the implant. In some embodiments, the implants include Oxy133.

In some embodiments, the implant includes oxysterols which aid in osteogenesis. In some embodiments, the implant or matrix includes Oxy34, Oxy49, and/or Oxy133. In some embodiments, the implant includes an oxysterol comprising the structure:

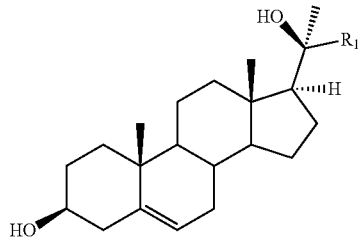

or a pharmaceutically acceptable salt, hydrate or solvate thereof, wherein R1 comprises an aliphatic or cyclic substituent having at least one carbon atom.

In some embodiments, R comprises an alkyl, a heteroalkyl, an alkanyl, a heteroalkanyl, an alkenyl, a heteroalkenyl, an alkynyl, a heteroalkanyl, an alkyldiyl, a heteroalkyldiyl, an alkyleno, a heteroalkyleno, an aryl, an aryldiyl, an arydeno, an arylaryl, a biaryl, an arylalkyl, a heteroaryl, a heteroaryldiyl, a heteroaryleno, a heteroaryl-heteroaryl, a biheteroaryl, a heteroarylalkyl or combinations thereof. In some embodiments, the R substituent comprises a (C1-C20) alkyl or heteroalkyl, a ($C_2$-$C_{20}$) aryl or heteroaryl, a ($C_6$-$C_{26}$) arylalkyl or heteroalkyl and a ($C_5$-$C_{20}$) arylalkyl or heteroaryl-heteroalkyl, a ($C_4$-$C_{10}$) alkyldiyl or heteroalkyldiyl, or a ($C_4$-$C_{10}$) alkyleno or heteroalkyleno. The R substituent may be cyclic or acyclic, branched or unbranched, substituted or unsubstituted, aromatic, saturated or unsaturated chains, or combinations thereof. In some embodiments, the R substituent is an aliphatic group. In some embodiments, the R substituent is a cyclic group. In some embodiments, the R substituent is a hexyl group.

In some embodiments, the present disclosure can include an implant including an osteogenic oxysterol (e.g., Oxy133) and its ability to promote osteogenic differentiation in vitro. Oxy133 is a particularly effective osteogenic agent. In various applications, Oxy133 is useful in treating conditions that would benefit from localized stimulation of bone formation, such as, for example, spinal fusion, fracture repair, bone regenerative/tissue applications, augmentation of bone density in the jaw for dental implants, osteoporosis or the like. One particular advantage of Oxy133 is that it provides greater ease of synthesis and improved time to fusion when compared to other osteogenic oxysterols. Oxy133 is a small molecule that can serve as an anabolic therapeutic agent for bone growth, as well as a useful agent for treatment of a variety of other conditions.

In some embodiments, the implant include Oxy133, having the formula:

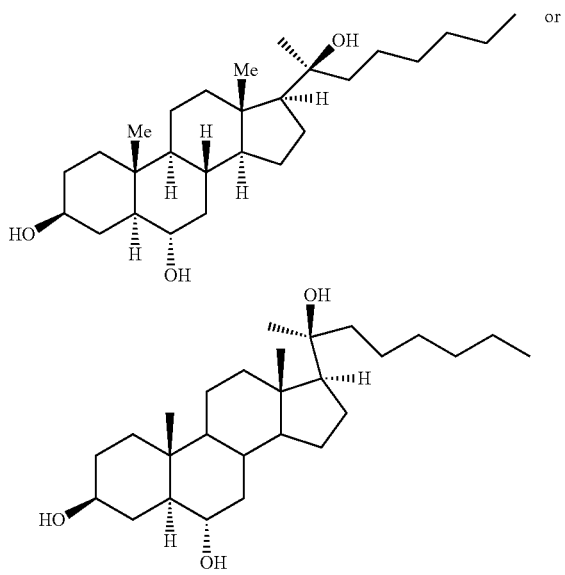

or a pharmaceutically acceptable salt, solvate or hydrate thereof. The Oxy133 may be used as a bioactive or pharmaceutical composition comprising Oxy133 or a pharmaceutically acceptable salt, solvate or hydrate thereof. Oxy133 has the IUPAC designation (3S,5S,6S,8R,9S,10R, 13S,14S,17S)-17-((S)-2-hydroxyoctan-2-yl)-10,13-dimethylhexadecahydro-1H-cyclopenta[a]phenanthrene-3,6-diol.

In some embodiments, the dosage of Oxy133 is from approximately 10 pg/day to approximately 80 g/day. In some embodiments, the dosage of Oxy133 is from approximately 1.0 g/day, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, 40.0, 40.5, 41.0, 41.5, 42.0, 42.5, 43.0, 43.5, 44.0, 44.5, 45.0, 45.5, 46.0, 46.5, 47.0, 47.5, 48.0, 48.5, 49.0, 49.5 50.0, 50.5, 51.0, 51.5, 52.0, 52.5, 53.0, 53.5, 54.0, 54.5, 55.0, 55.5, 56.0, 56.5, 57.0, 57.5, 58.0, 58.5, 59.0, 59.5 to about 60.0 grams/day. Additional dosages of Oxy133 include from approximately 2.4 ng/day to approximately 50 mg/day; approximately 50 ng/day to approximately 2.5 mg/day; approximately 250 ng/day to approximately 250 mcg/day; approximately 250 ng/day to approximately 50 mcg/day; approximately 250 ng/day to approximately 25 mcg/day; approximately 250 ng/day to approximately 1 mcg/day; approximately 300 ng/day to approximately 750 ng/day or approximately 0.50 mcg/day to 500 ng/day. In various embodiments, the dose may be about 0.01 to approximately 10 mcg/day or approximately 1 ng/day to about 120 mcg/day. In some embodiments, the dosage of Oxy133 is in greater amounts. For example, in some embodiments, the dosage of Oxy133 is from 0.01 mg/day to 5 g/day.

The implant can comprise the oxysterol (e.g., Oxy133) disposed homogenously throughout it or in discrete regions. In some embodiments, the oxysterol is either uniformly distributed or non-uniformly throughout the implant. The oxysterol can be loaded in the implant and can comprise from about 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, 40.0, 40.5, 41.0, 41.5, 42.0, 42.5, 43.0, 43.5, 44.0, 44.5, 45.0, 45.5, 46.0, 46.5, 47.0, 47.5, 48.0, 48.5, 49.0, 49.5, 50.0, 50.5, 51.0, 51.5, 52.0, 52.5, 53.0, 53.5, 54.0, 54.5, 55.0, 55.5, 56.0, 56.5, 57.0, 57.5, 58.0, 58.5, 59.0, 59.5 to about 60% w/v, w/w and/or v/v of the total weight of the implant.

In some embodiments, the oxysterol can be loaded into the implant and comprises from about 5 wt % to about 80 wt or from about 5 wt % to about 90 wt. In some embodiments, a high concentration of the oxysterol can be loaded into the implant and comprises from about 20 wt % to about 99 wt % of the implant. In some embodiments, the oxysterol can be loaded into the implant in an amount from about 50 wt % to about 90 wt % of the implant. In some embodiments, the oxysterol can be loaded into the implant in an amount of about 20 wt % to about 30 wt %, about 30 wt % to about 40 wt %, about 40 wt % to about 50 wt %, about 50 wt % to about 60 wt %, about 60 wt % to about 70 wt %, about 70 wt % to about 80 wt %, about 80 wt % to about 90 wt %, or about 90 wt % to about 99 wt %. In some embodiments, the oxysterol can be loaded into the implant in an amount of from about 20, 25, 30, 35, 40, 45, 50, 55, 60, 65, 70, 75, 80, 85, 90, 95, to about 99 wt % of the implant.

The oxysterol can be loaded in the implant and can comprise from about 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, 40.0, 40.5, 41.0, 41.5, 42.0, 42.5, 43.0, 43.5, 44.0, 44.5, 45.0, 45.5, 46.0, 46.5, 47.0, 47.5, 48.0, 48.5, 49.0, 49.5, 50.0, 50.5, 51.0, 51.5, 52.0, 52.5, 53.0, 53.5, 54.0, 54.5, 55.0, 55.5, 56.0, 56.5, 57.0, 57.5, 58.0, 58.5, 59.0, 59.5 to about 60 mg/cc of the implant. In some embodiments, the oxysterol can be loaded into the implant in an amount of about 400 mg/cc. In some embodiments, the oxysterol can be loaded into the implant in an amount of about 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, to about 500 mg/cc.

In addition to the compound Oxy133, other embodiments of the disclosure encompass any and all individual stereoisomers at any of the stereocenters present in Oxy133, including diastereomers, racemates, enantiomers, and other isomers of the compound. In embodiments of the disclosure, Oxy133 may include all polymorphs, solvates or hydrates of the compound, such as hydrates and those formed with organic solvents.

The ability to prepare salts depends on the acidity or basicity of a compound. Suitable salts of the compound include, but are not limited to, acid addition salts, such as those made with hydrochloric, hydrobromic, hydroiodic, perchloric, sulfuric, nitric, phosphoric, acetic, propionic, glycolic, lactic, pyruvic, malonic, succinic, maleic, fumaric, malic, tartaric, citric, benzoic, carbonic cinnamic, mandelic, methanesulfonic, ethanesulfonic, hydroxyethanesulfonic, benezenesulfonic, p-toluene sulfonic, cyclohexanesulfamic, salicyclic, p-aminosalicylic, 2-phenoxybenzoic, and 2-acetoxybenzoic acid; salts made with saccharin; alkali metal salts, such as sodium and potassium salts; alkaline earth metal salts, such as calcium and magnesium salts; and salts formed with organic or inorganic ligands, such as quaternary ammonium salts. Additional suitable salts include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate salts of the compounds.

In various embodiments, Oxy133 includes one or more biological functions. That is, Oxy133 can induce a biological response when contacted with a mesenchymal stem cell or a bone marrow stromal cell. For example, Oxy133 may stimulate osteoblastic differentiation. In some embodiments, a bioactive composition including Oxy133 may include one or more biological functions when administered to a mammalian cell, for example, a cell in vitro or a cell in a human or an animal. For example, such a bioactive composition may stimulate osteoblastic differentiation. In some embodiments, such a biological function can arise from stimulation of the hedgehog pathway.

In some embodiments, one of more biologically active ingredients may be added to the implant. These active ingredients may or may not be related to the bone repair capabilities of the composition. Suitable active ingredients hemostatic agents, bone morphogenic proteins (BMPs), genes, growth differentiation factors (GDFs), or other non-collagenic proteins such as TGF-β, PDGF, ostropontin, osteonectin, cytokines, and the like.

In one embodiment, the implant may include at least one BMPs, which are a class of proteins thought to have osteoinductive or growth-promoting activities on endogenous bone tissue, or function as pro-collagen precursors. Known members of the BMP family include, but are not limited to, BMP-1, BMP-2, BMP-3, BMP-4, BMP-5, BMP-6, BMP-7, BMP-8, BMP-9, BMP-10, BMP-11, BMP-12, BMP-13, BMP-15, BMP-16, BMP-17, BMP-18 as well as polynucleotides or polypeptides thereof, as well as mature polypeptides or polynucleotides encoding the same.

BMPs utilized as osteoinductive agents comprise one or more of BMP-1; BMP-2; BMP-3; BMP-4; BMP-5; BMP-6; BMP-7; BMP-8; BMP-9; BMP-10; BMP-11; BMP-12; BMP-13; BMP-15; BMP-16; BMP-17, or BMP-18; as well as any combination of one or more of these BMPs, including full length BMPs or fragments thereof, or combinations thereof, either as polypeptides or polynucleotides encoding the polypeptide fragments of all of the recited BMPs. The isolated BMP osteoinductive agents may be administered as polynucleotides, polypeptides, full length protein or combinations thereof.

In another embodiment, the particles may include one or more Growth Differentiation Factors ("GDFs") disposed in the compartment or disposed on or in the coherent mass. Known GDFs include, but are not limited to, GDF-1, GDF-2, GDF-3, GDF-7, GDF-10, GDF-11, and GDF-15. For example, GDFs useful as isolated osteoinductive agents include, but are not limited to, the following GDFs: GDF-1 polynucleotides or polypeptides corresponding to GenBank Accession Numbers M62302, AAA58501, and AAB94786, as well as mature GDF-1 polypeptides or polynucleotides encoding the same. GDF-2 polynucleotides or polypeptides corresponding to GenBank Accession Numbers BC069643, BC074921, Q9UK05, AAH69643, or AAH74921, as well as mature GDF-2 polypeptides or polynucleotides encoding the same. GDF-3 polynucleotides or polypeptides corresponding to GenBank Accession Numbers AF263538, BC030959, AAF91389, AAQ89234, or Q9NR23, as well as mature GDF-3 polypeptides or polynucleotides encoding the same. GDF-7 polynucleotides or polypeptides corresponding to GenBank Accession Numbers AB158468, AF522369, AAP97720, or Q7Z4P5, as well as mature GDF-7 polypeptides or polynucleotides encoding the same. GDF-10 polynucleotides or polypeptides corresponding to GenBank Accession Numbers BC028237 or AAH28237, as well as mature GDF-10 polypeptides or polynucleotides encoding the same.

GDF-11 polynucleotides or polypeptides corresponding to GenBank Accession Numbers AF100907, NP005802 or 095390, as well as mature GDF-11 polypeptides or polynucleotides encoding the same. GDF-15 polynucleotides or polypeptides corresponding to GenBank Accession Numbers BC008962, BC000529, AAH00529, or NP004855, as well as mature GDF-15 polypeptides or polynucleotides encoding the same.

In some embodiments, the implant contains other bioactive agents which can be delivered with materials of the disclosure. In certain embodiments, the bioactive agent is a drug. These bioactive agents may include, for example, antimicrobials, antibiotics, antimyobacterial, antifungals, antivirals, antineoplastic agents, antitumor agents, agents affecting the immune response, blood calcium regulators, agents useful in glucose regulation, anticoagulants, antithrombotics, antihyperlipidemic agents, cardiac drugs, thyromimetic and antithyroid drugs, adrenergics, antihypertensive agents, cholinergic, anticholinergics, antispasmodics, antiulcer agents, skeletal and smooth muscle relaxants, prostaglandins, general inhibitors of the allergic response, antihistamines, local anesthetics, analgesics, narcotic antagonists, antitussives, sedative-hypnotic agents, anticonvulsants, antipsychotics, anti-anxiety agents, antidepressant agents, anorexigenics, non-steroidal anti-inflammatory agents, steroidal anti-inflammatory agents, antioxidants, vaso-active agents, bone-active agents, osteogenic factors, antiarthritics, and diagnostic agents.

A more complete listing of bioactive agents and specific drugs suitable for use in the present disclosure may be found in "The Merck Index: An Encyclopedia of Chemicals, Drugs, and Biologicals," Edited by Susan Budavari, et al.; and the United States Pharmacopoeia/National Formulary XXXVII/XXXII, published by the United States Pharmacopeial Convention, Inc., Rockville, Md., 2013, each of which is incorporated herein by reference.

Bioactive agents may also be provided by incorporation into the implantable composition. Bioactive agents such as those described herein can be incorporated homogeneously or regionally into the implant material by simple admixture or otherwise.

Further, they may be incorporated via a medium such as microspheres or another microparticulate formulation. Suitable techniques for forming microparticles are well known in the art, and can be used to entrain or encapsulate bioactive agents, whereafter the microparticles may be dispersed within the bone graft composite upon or after its preparation.

It will be appreciated that the amount of additive used will vary depending upon the type of additive, the specific activity of the particular additive preparation employed, and the intended use of the composition. The desired amount is readily determinable by the user.

Any of a variety of medically and/or surgically useful substances can be incorporated in, or associated with, the bone material either before, during, or after preparation of the implantable composition. Thus, for example when the bone material is used, one or more of such substances may be introduced into the bone fibers, for example, by soaking or immersing these bone fibers in a solution or dispersion of the desired substance(s).

In some embodiments, the implant bone fibers can be lyophilized with one or more growth factors (e.g., BMP, GDF, etc.), drugs so that it can be released from the implant in a sustained release manner.

In some embodiments, after the implant is formed, a binding agent may be added to it before implantation. However, in some embodiments, the DBM fibers of the implant do not contain a binding agent and it stays together without the use of a binding agent. Examples of suitable binding agents that optionally can be included after the implant is formed include, but are not limited to: (i) polyhydroxy compound, for example, such classes of compounds as the acyclic polyhydric alcohols, non-reducing sugars, sugar alcohols, sugar acids, monosaccharides, disaccharides, water-soluble or water dispersible oligosaccharides, polysaccharides and known derivatives of the foregoing. Specific polyhydroxy compounds include, 1,2-propanediol, glycerol, 1,4,-butylene glycol trimethylolethane, trimethylolpropane, erythritol, pentaerythritol, ethylene glycols, diethylene glycol, triethylene glycol, tetraethylene glycol, propylene glycol, dipropylene glycol; polyoxyethylene-polyoxypropylene copolymer, for example, of the type known and commercially available under the trade names Pluronic and Emkalyx; polyoxyethylene-polyoxypropylene block copolymer, for example, of the type known and commercially available under the trade name Poloxamer; alkylphenolhydroxypolyoxyethylene, for example, of the type known and commercially available under the trade name Triton, polyoxyalkylene glycols such as the polyethylene glycols, xylitol, sorbitol, mannitol, dulcitol, arabinose, xylose, ribose, adonitol, arabitol, inositol, fructose, galactose, glucose, mannose, sorbose, sucrose, maltose, lactose, maltitol, lactitol, stachyose, maltopentaose, cyclomaltohexaose, carrageenan, agar, dextran, alginic acid, guar gum, gum tragacanth, locust bean gum, gum arabic, xanthan gum, amylose, mixtures of any of the foregoing.

Useful agents include solvents such as dichloromethane, trichloroacetic acid, acetonitrile and acids such as trifluoroacetic acid and hydrogen fluoride. In some embodiments, a lubricant, such as water or polyethylene glycol may be added.

In some embodiments, the implant containing the fibers may also contain other beneficial substances including for example preservatives, cosolvents, suspending agents, viscosity enhancing agents, ionic strength and osmolality adjusters and/or other excipients. Suitable buffering agents can also be used and include but are not limited to alkaline earth metal carbonates, phosphates, bicarbonates, citrates, borates, acetates, succinates, or others. Illustrative-specific buffering agents include for instance sodium phosphate, sodium citrate, sodium borate, sodium acetate, sodium bicarbonate, sodium carbonate, and sodium tromethanine (TRIS).

In some embodiments, the bone fibers of the implant may be mixed with a porogen material which is later removed during manufacturing to enhance porosity of the dried cohesive mass. Suitable porogen materials may be made of any biocompatible, biodegradable substance that can be formed into a particle and that is capable of at least substantially retaining its shape during the manufacturing of the implant, but is later removed or degrades or dissolves when placed in contact with an aqueous solution, or other liquid. The porogens, in some embodiments, may be inorganic or organic, for example, they may be made from gelatin, an organic polymer (e.g., polyvinyl alcohol), polyurethanes, polyorthoesters, PLA, PGA, and PLGA copolymers, a saccharide, a calcium salt, sodium chloride, calcium phosphate or mixtures thereof. Porogen particles may be about 100 to about 500 microns.

In one embodiment, all porogen particles of a given morphology can have at least one average axial, transverse, or lateral dimension that is about 100 to about 500 microns. In some embodiments, all porogen particles used can independently have at least one axial, transverse, or lateral dimension that is about 100 to about 500 microns. In some embodiments, all porogen particles used can collectively have at least one average axial, transverse, or lateral dimension that is about 100 to about 500 microns. In some embodiments, at least one dimension of the porogen particles can be about 100 microns or more, or about 120 microns or more, or about 140 microns or more. In some embodiments, at least one dimension of the porogen particles can be about 500 microns or less, about 425 microns or less, about 350 microns or less, about 300 microns or less, or about 250 microns or less. In some embodiments, the porogen particles can have at least one dimension that is about 120 to about 400 microns.

In some embodiments, the implant contains single or multiple concentrations of size controlled fibers to affect the consistency of the implant and affect the handling of the implant after hydration.

In some instances the fibers may be mixed with particles in the implant to affect the consistency of the implant and affect the handling of the implant after hydration.

In some instances multiple implants might be packaged together to improve hydration and or handling of the implants prior to and after hydration.

In some instances the implant may be hydrated with a polar or non-polar solutions and/or salt solutions prior to drying to enhance later rehydration of the implant.

DBM Fiber

The present disclosure also provides methods for shaping the implant comprising fibers as shown, in FIGS. 3-11.

FIG. 3 depicts mineralized fibers having increased surface area. The fibers are milled from bone shafts using any appropriate apparatus, such as a cartridge mill. The fibers are milled to include curled shapes having frayed portions and/or hooked portions to facilitate mechanical interlocking of the fibers. For example, as shown in FIG. 3, milling the bone material creates fibers 74 and bone particles 76 separate from the fiber. The shape of the allograft may be tailored to fit the site at which it is to be situated. For example, it may be in the shape of a morsel, a plug, a pin, a peg, a cylinder, a block, a wedge, ring, a sheet, etc.

In one embodiment, the method comprises placing allograft bone fibers into a mold prior to demineralization and/or lyophilization. The fibers are then demineralized, sterilized and/or lyophilized to create a shaped implant, as shown in FIGS. 3-11. The fibers can be placed into a mold and then subjected to demineralization and/or lyophilization to make the desired shape or the fibers can be demineralization and/or lyophilization and then shaped by stamping or punching the desired shape. The demineralization and lyophilization steps alter the shape of the fibers to facilitate entanglement and mechanical interlocking, as discussed herein. Thus, in some embodiments, the fibers are shaped into a coherent mass through being subjected to demineralization and/or lyophilization while in a molded cavity (not shown). The fibers form such a coherent mass without the use of a binding agent or carrier.

In some embodiments, the fibers are placed into molds and shaped to form an implant in a range of predetermined shapes and sizes according to the needs of a medical procedure. In some embodiments, the implant may be made by injection molding, compression molding, die pressing, slip casting, laser cutting, water-jet machining, sand casting, shell mold casting, lost tissue scaffold casting, plaster-mold casting, vacuum casting, permanent-mold casting, slush casting, pressure casting, die casting, centrifugal casting, squeeze casting, rolling, forging, swaging, extrusion, shearing, spinning, or combinations thereof.

Figure 6:
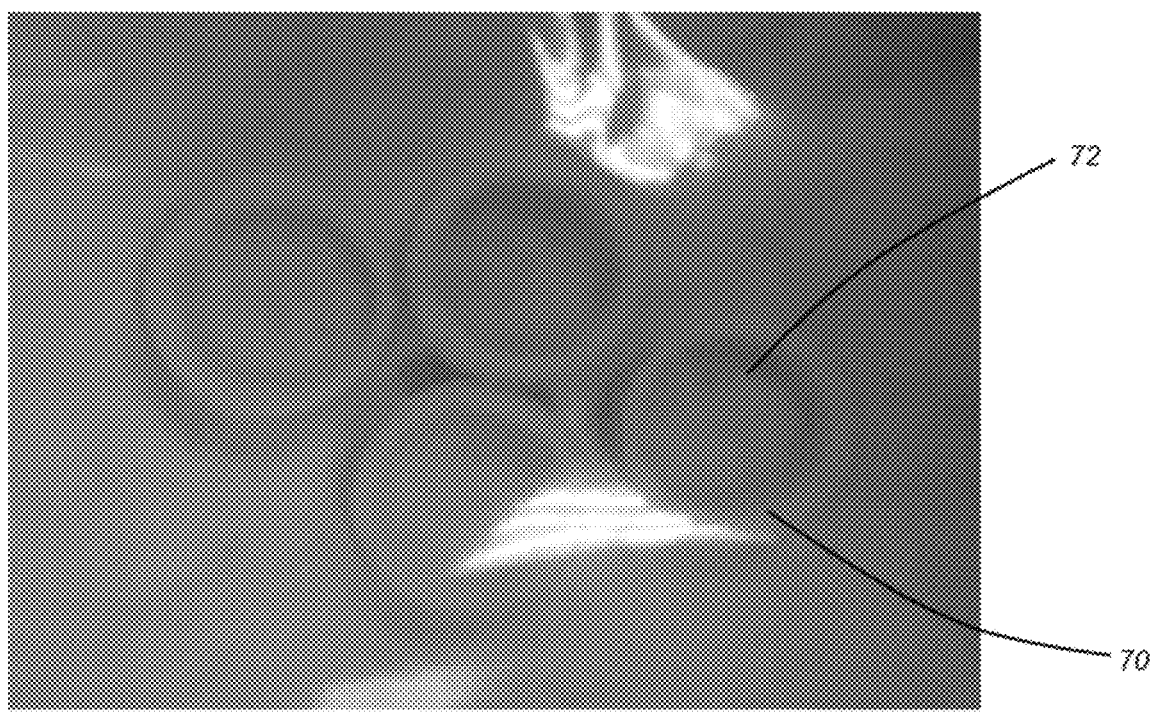
FIG. 6 depicts the bone material in a disc shape unit. Similarly to the coherent mass in FIG. 7, coherent mass is formed after demineralization and then placing the fibers in a mold and then lyophilization. Alternatively, the coherent mass can be punched or stamped into the desired shape and then lyophilized or lyophilized after demineralization and then punched or stamped into the desired shape. The coherent mass is in a disc shape and includes a reservoir to facilitate hydration.

The fibers may be molded into a disc shaped implant 70 having a reservoir 72 to facilitate hydration, as shown in FIG. 6. Implant 70 may include a uniform thickness or a variable thickness across its surface to facilitate packaging and/or hydration. Reservoir 72 comprises a depressed area on a surface of implant 70 to hold liquid during hydration. As shown in FIG. 6, reservoir 72 comprises a circular shape. However, in other embodiments, the reservoir may include variable cross sectional shapes, such as polygonal, oval or irregular.

Figure 7:
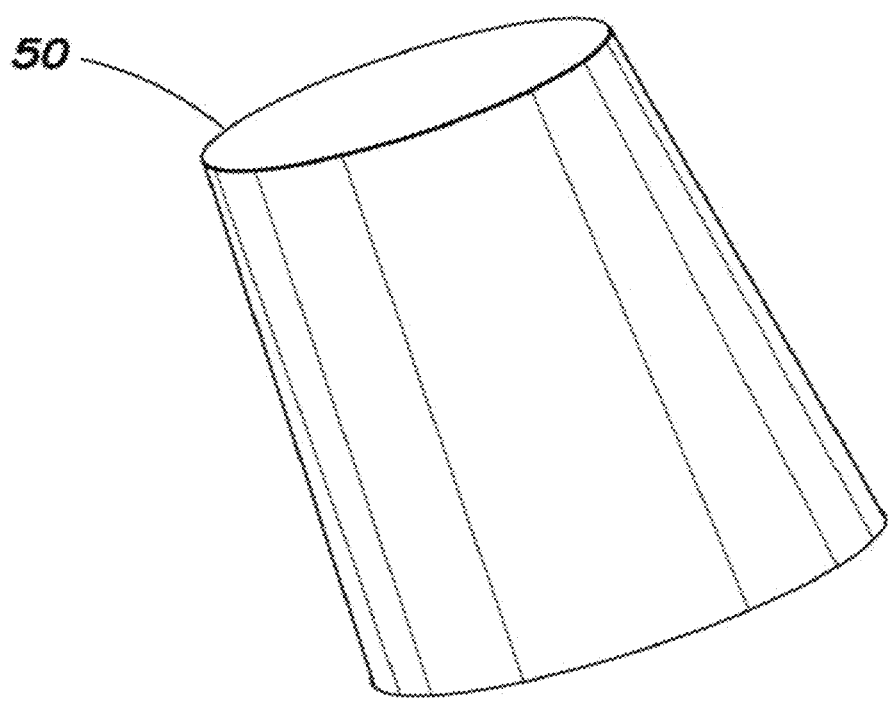
FIG. 7 depicts the bone material in a plug shape.

The fibers may be molded into a conical or plug shape to form a second implant 50, as shown in FIG. 7. Second implant 50 includes a first end having a first diameter and a second end having a second diameter. In some embodiments, the first diameter is wider than the second diameter.

Figure 8:
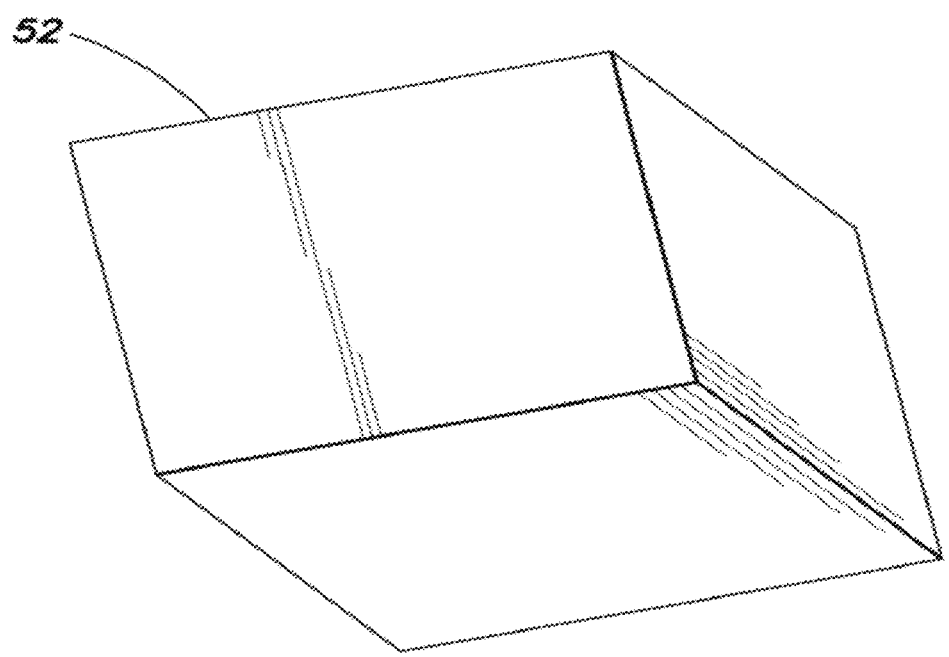
FIG. 8 depicts the bone material in a cube shape.

The fibers may be molded into a cube shape to form a third implant 52, as shown in FIG. 8. In other embodiments, the implant may include other prismatic configurations, similar to third implant 52. For example, the implant may be rectangular, pyramidal, triangular, pentagonal, or other polygonal or irregular prismatic shapes.

Figure 9:
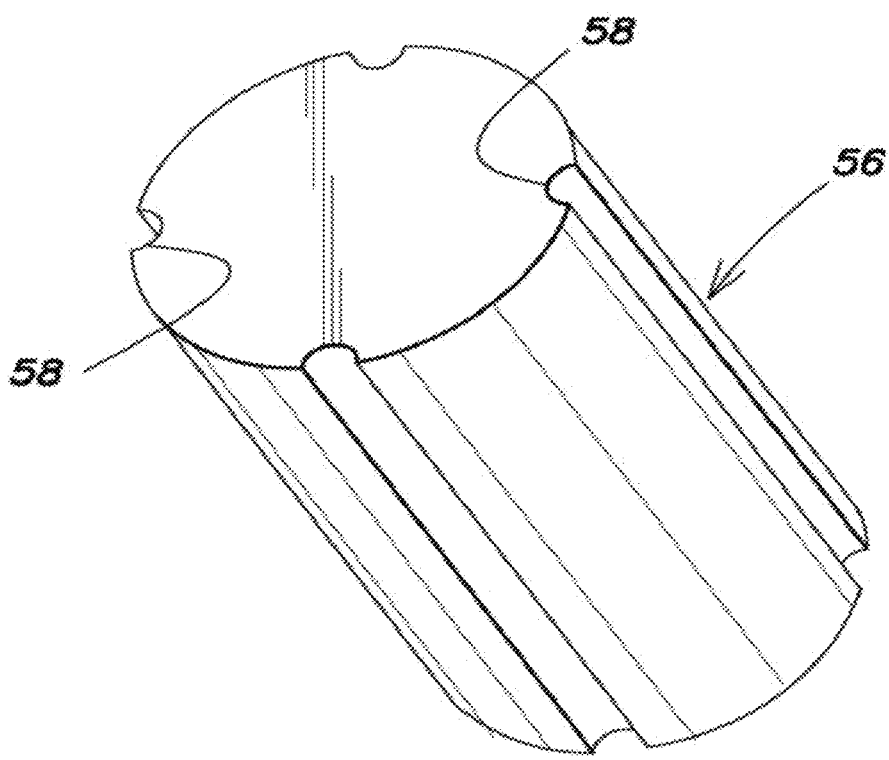
FIG. 9 depicts the bone material in a cylindrical shape having hydration channels to facilitate hydration.

The fibers may be molded into a cylindrical shape to form a fourth implant 56, as shown in FIG. 9. Fourth implant 56 includes a first end having a first diameter and a second end having a second diameter. In some embodiments, the first diameter is the same as the second diameter.

The fibers may be molded into a cylindrical shape to form implant 56 that has external hydration channels 58, as shown in FIG. 9. Fourth implant 56 includes a first end having a first diameter and a second end having a second diameter. In some embodiments, the first diameter is wider than or the same size as the second diameter. Hydration channels 58 are present on an outer surface of fifth implant 56 and are configured to facilitate entrance of a hydrating liquid into fifth implant 56, as discussed herein. External hydration channels 58 include a rounded inner surface formed from drilling or pressing. However, in other embodiments, channels 58 may be slotted and include straight inner surfaces. The fibers are porous and the liquid can pass through the coherent mass, however, hydration channels 58 enhance the passage of fluid.

Figure 10:
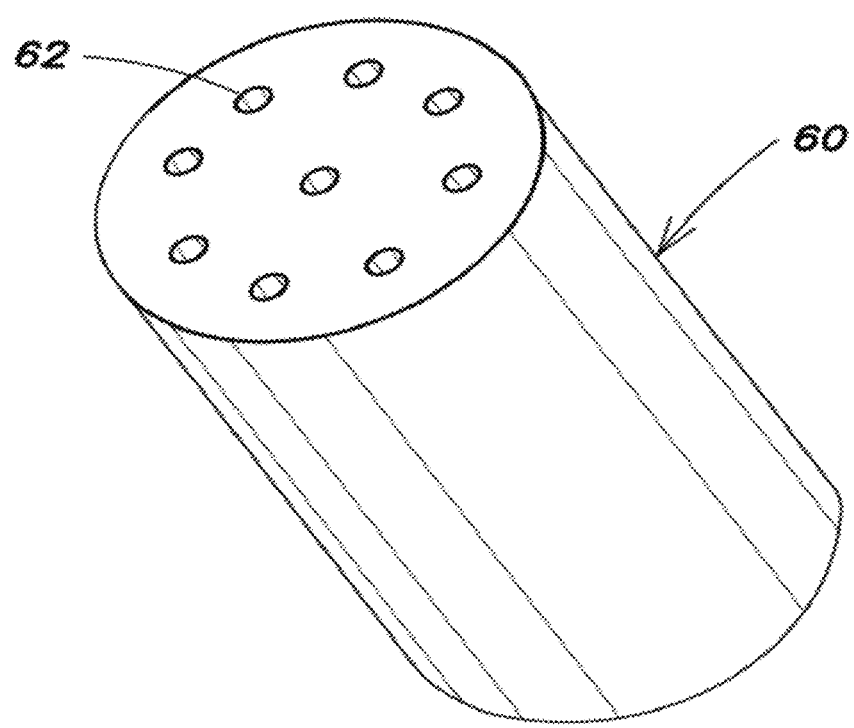
FIG. 10 depicts the bone material in a cylindrical shape. The bone material includes internal hydration channels to facilitate hydration.

The fibers may be molded into a cylindrical shape to form a coherent mass 60 that has internal hydration channels 62, as shown in FIG. 10. Coherent mass 60 includes a first end having a first diameter and a second end having a second diameter. In some embodiments, the first diameter is wider than or the same size as the second diameter. Hydration channels 62 extend through at least a portion of coherent mass 60 and are configured to facilitate entrance of a hydrating liquid into coherent mass 60, as discussed herein. Internal hydration channels 62 include a rounded inner surface formed from drilling or pressing. The fibers are porous and the liquid can pass through the coherent mass, however, hydration channels 62 enhance the passage of fluid into the implant.

Figure 11:
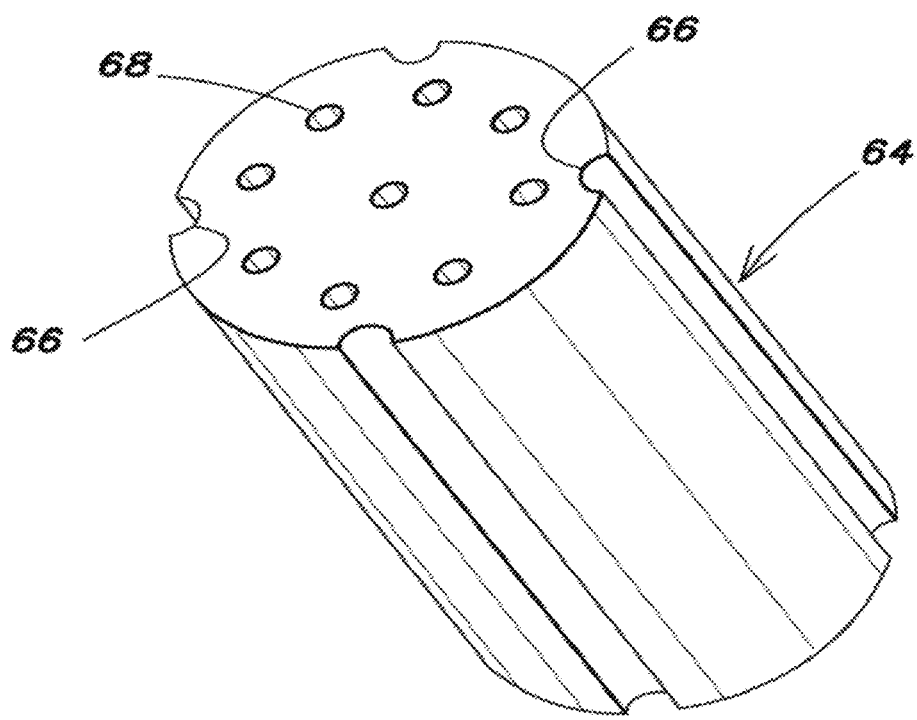
FIG. 11 depicts the bone material in a cylindrical shape. The bone material includes a combination of external hydration channels and internal hydration channels to facilitate hydration of coherent mass.

The fibers may be molded into a conical or plug shape to form a coherent mass 64 that has external hydration channels 66 and internal hydration channels 68, as shown in FIG. 11. Coherent mass 64 includes a first end having a first diameter and a second end having a second diameter. In some embodiments, the first diameter is wider than or the same as the second diameter. External hydration channels 66 are present on an outer surface of coherent mass 64, and internal hydration channels 68 extend through at least a portion of coherent mass 64. Hydration channels 66, 68 are configured to facilitate entrance of a hydrating liquid into coherent mass 64, as discussed herein. Hydration channels 66, 68 include a rounded inner surface formed from drilling or pressing.

Demineralization

After the bone is obtained from the donor and milled into a fiber, it is processed, e.g., cleaned, disinfected, defatted, etc., using methods well known in the art. The entire bone can then be demineralized or, if desired, the bone can just be sectioned before demineralization. The entire bone or one or more of its sections is then subjected to demineralization in order to reduce the inorganic content to a low level, e.g., to contain less than about 10% by weight, preferably less than about 5% by weight and more preferably less than about 1% by weight, residual calcium.

DBM may be prepared in any suitable manner. In one embodiment, the DBM is prepared through the acid extraction of minerals from bone. It includes the collagen matrix of the bone together with acid insoluble proteins including bone morphogenic proteins (BMPs) and other growth factors. It can be formulated for use as granules, gels, sponge material or putty and can be freeze-dried for storage. Sterilization procedures, such as electron beam radiation, are used to protect the implant from disease transmission and may reduce the activity of beneficial growth factors in the DBM. DBM provides an initial osteoconductive matrix and exhibits a degree of osteoinductive potential, inducing the infiltration and differentiation of osteoprogenitor cells from the surrounding tissues. As noted, in embodiments of bone particles taken from cortical long bones, the osteoinductive potential of the bone particles when demineralized may vary based on the source of the bone particles, whether from the periosteal layer, the middle layer, or the endosteal layer.

DBM preparations have been used for many years in orthopedic medicine to promote the formation of bone. For example, DBM has found use in the repair of fractures, in the fusion of vertebrae, in joint replacement surgery, and in treating bone destruction due to underlying disease such as rheumatoid arthritis. DBM is thought to promote bone formation in vivo by osteoconductive and osteoinductive processes. The osteoinductive effect of implanted DBM compositions is thought to result from the presence of active growth factors present on the isolated collagen-based matrix. These factors include members of the TGF-β, IGF, and BMP protein families. Particular examples of osteoinductive factors include TGF-β, IGF-1, IGF-2, BMP-2, BMP-7, parathyroid hormone (PTH), and angiogenic factors. Other osteoinductive factors such as osteocalcin and osteopontin are also likely to be present in DBM preparations as well. There are also likely to be other unnamed or undiscovered osteoinductive factors present in DBM.

In one demineralization procedure, the bone is subjected to an acid demineralization step followed by a defatting/disinfecting step, where a coherent mass of bone fibers can be formed. The bone is immersed in acid to effect demineralization. Acids that can be employed in this step include inorganic acids such as hydrochloric acid and as well as organic acids such as formic acid, acetic acid, peracetic acid, citric acid, propionic acid, etc. The depth of demineralization into the bone surface can be controlled by adjusting the treatment time, temperature of the demineralizing solution, concentration of the demineralizing solution, and agitation intensity during treatment. Thus, in various embodiments, the DBM may be fully demineralized, partially demineralized, or surface demineralized.

The demineralized bone is rinsed with sterile water and/or buffered solution(s) to remove residual amounts of acid and thereby raise the pH. A suitable defatting/disinfectant solution is an aqueous solution of ethanol, the ethanol being a good solvent for lipids and the water being a good hydrophilic carrier to enable the solution to penetrate more deeply into the bone particles. The aqueous ethanol solution also disinfects the bone by killing vegetative microorganisms and viruses. Ordinarily, at least about 10 to 40 percent by weight of water (i.e., about 60 to 90 weight percent of defatting agent such as alcohol) is present in the defatting disinfecting solution to produce optimal lipid removal and disinfection within a given period of time. A suitable concentration range of the defatting solution is from about 60 to about 85 weight percent alcohol, or about 70 weight percent alcohol.

In some embodiments, the demineralized bone may be further treated to effect properties of the bone. For example, the DBM may be treated to disrupt the collagen structure of the DBM. Such treatment may comprise collagenase treatment, heat treatment, mechanical treatment, or other. Reference is made to U.S. Provisional Patent Applications 60/944,408, 60/944,417, and 60/957,614, herein incorporated by reference, for further treatment options.

Alternative Drying Methods

In some embodiments, the bone fibers are dried under vacuum conditions at ambient temperature or elevated temperature. In various embodiments, the bone fibers are dried at ambient pressure at ambient temperature or elevated temperature.

In some embodiments, the bone fibers are lyophilized either in a mold for a desired shape or out of a mold, where in can be shaped (e.g., stamped, punched, cut, etc.). For example, the bottle containing bone and conserving agent is initially frozen to −76° C. with the bone and conserving agent later being subjected to a vacuum of less than 100 militorr while the temperature is maintained at or below −35° C. The end point of the lyophilization procedure is the determination of residual moisture of approximately 0%-20%. Once the bone has been lyophilized, it is stored in sealed, vacuum-contained, bottles prior to its reconstitution and use.

In some embodiments, the demineralization and lyophilization steps alter the shape of the fibers to facilitate entanglement and mechanical interlocking. Thus, in some embodiments, the fibers are shaped into a coherent mass through being subjected to demineralization and/or lyophilization while in a molded cavity (not shown). The fibers form such a coherent mass without the use of a binding agent or carrier. For example, as shown in FIG. 4, the individual fibers 82 form a coherent mass 78 after the demineralization and lyophilization steps. During lyophilization of fibers 82, frayed/hooked portions 80 become increasingly tangled with each other to increase mechanical interlocking of the fibers.

To facilitate on-site preparation and/or usage of the composition herein, the demineralized fibrous bone elements and non-fibrous bone elements, preferably in lyophilized or frozen form, can be stored in separate packages or containers under sterile conditions and brought together in intimate admixture at the moment of use for immediate application to an osseous defect site employing any suitable means such as spatula, forceps, syringe, tamping device, and the like. Alternatively, the implant can be prepared well in advance and stored under sterile conditions until required for use. When the implant is prepared well in advance it is preferably lyophilized prior to packaging for storage. In some embodiments, the composition described herein can be combined with autograft bone marrow aspirate, autograft bone, preparations of selected autograft cells, autograft cells containing genes encoding bone promoting action prior to being placed in a defect site. In various embodiments, the implant is packaged and ready for use in a suitable container, such as for example, a resealable non-toxic bottle, a bag mesh or pouch or is provided as a kit which can be prepared at a surgeon's direction when needed.

Hydration

Figure 5:
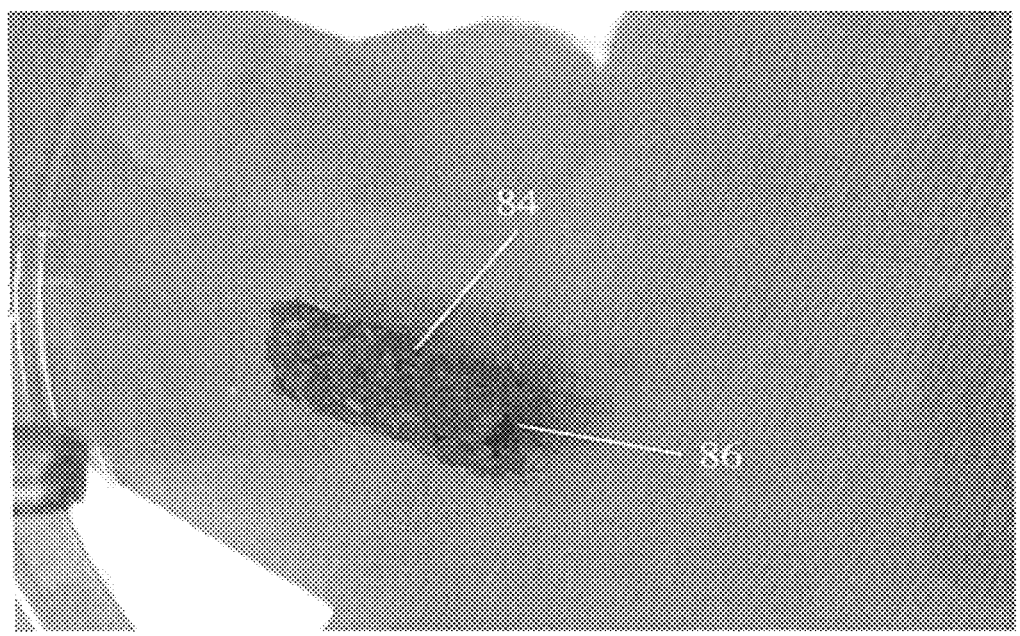
FIG. 5 depicts the bone material in a cylindrical shape. After the bone fibers are milled, the fibers are demineralized and subsequently placed into a mold or punch and lyophilized to form a coherent mass in a cylindrical shape having a hydration channel. The coherent mass may be hydrated by a liquid such as blood, water or saline.

As shown, for example, in FIG. 5, following demineralization, lyophilization and/or electron beam radiation, the implant is hydrated to turn the implant into a moldable and malleable putty. In some embodiments, the implant is hydrated with water, saline and/or blood, bone marrow aspirate, bone marrow aspirate concentrates, or other blood fractions and/or solutions made from blood. Once hydrated, the implant is placed into a surgical site at a location determined by a medical practitioner. The fibers in the implant maintain their coherency and mechanical interactions such that the putty requires no binding agent or carrier when placed in situ.

In some embodiments, the implant may be hydrated with PBS or other physiologically acceptable fluid, and provided for use in a hydrated form. The implant may be placed at a surgical site directly and subsequently hydrated, or it can be hydrated to form a wet paste and subsequently implanted at a surgical site.

A physiologically acceptable liquid, in some embodiments containing water, may be added to the bone repair implant prior to placement into the site or defect. Such physiologically acceptable liquids include those discussed above, including physiological saline or a blood product. Blood products include whole blood and blood fractions such as platelet rich plasma and platelet poor plasma.

In some embodiments, the implant is hydrated with a physiologically acceptable liquid. Non-limiting examples of physiologically acceptable liquids include saline, phosphate buffered saline (PBS), hyaluronic acid, cellulose ethers (such as carboxymethyl cellulose), collagen, gelatin, autoclaved bone powder, osteoconductive carriers, whole blood, blood fractions, bone marrow aspirate, concentrated bone marrow aspirate, and mixtures thereof. Non-limiting examples of blood fractions include serum, plasma, platelet-rich plasma, concentrated platelet-rich plasma, platelet-poor plasma, and concentrated platelet poor plasma. After hydrating, the bone repair implant becomes a putty or a paste that can be molded into a predetermined shape or administered to a bone defect and manipulated to conform to the bone defect in such a manner that will promote healing. For example, the implant may be hydrated with about 2 ml of saline blood per 2.5 g of combined DBM and periosteal powder.

Methods of Treatment

Illustrative bone repair sites that can be treated with the implant of the disclosure include, for instance, those resulting from injury, defects brought about during the course of surgery, infection, malignancy or developmental malformation. The implant can be used in a wide variety of orthopedic, periodontal, neurosurgical and oral and maxillofacial surgical procedures including, but not limited to the repair of simple and compound fractures and non-unions; external and internal fixations; joint reconstructions such as arthrodesis; general arthroplasty; cup arthroplasty of the hip; femoral and humeral head replacement; femoral head surface replacement and total joint replacement; repairs of the vertebral column including spinal fusion and internal fixation; tumor surgery, e.g., deficit filing; discectomy; laminectomy; excision of spinal cord tumors; anterior cervical and thoracic operations; repairs of spinal injuries; scoliosis, lordosis and kyphosis treatments; intermaxillary fixation of fractures; mentoplasty; temporomandibular joint replacement; alveolar ridge augmentation and reconstruction; inlay osteoimplants; implant placement and revision: sinus lifts; cosmetic enhancement; etc. Specific bones which can be repaired or replaced with the implant include, but are not limited to the ethmoid; frontal; nasal; occipital; parietal; temporal; mandible; maxilla; zygomatic; cervical vertebra; thoracic vertebra; lumbar vertebra; sacrum; rib; sternum; clavicle; scapula; humerus; radius; ulna; carpal bones; metacarpal bones; phalanges; ilium; ischium; pubis; femur; tibia; fibula; patella; calcaneus; tarsal and metatarsal bones.

In accordance with certain aspects of the disclosure, the implant of the disclosure can be used as a bone void filler, or can be incorporated in, on or around a load bearing implant such as a spinal implant, hip implant (e.g. in or around an implant stem and/or behind an acetabular cup), and a knee implant (e.g. in or around a stem). In some embodiments, the implant of the disclosure can be incorporated in, on or around a load-bearing spinal implant device having a compressive strength of at least about 10000 N, such as a fusion cage, PEEK implants, dowel, or other device potentially having a pocket, chamber or other cavity for containing an osteoinductive composition, and used in a spinal fusion such as an interbody fusion. One illustrative such use is in conjunction with a load-bearing interbody spinal spacer to achieve interbody fusion. In these applications, the implant can be placed in and/or around the spacer to facilitate the fusion.

Methods for preparing DBM are well known in the art as described, e.g. U.S. Pat. Nos. 5,314,476, 5,507,813, 5,073,373, and 5,405,390, each incorporated herein by reference. Methods for preparing ceramic powders of calcium phosphate and/or hydroxyapatite are described, e.g., in U.S. Pat. Nos. 4,202,055 and 4,713,076, each incorporated herein by reference.

In some embodiments, the method comprises obtaining the fibers by shaving, milling, or pressing the sheet or block under aseptic conditions. The shape of the fibers can be optimized for inducing new bone formation and handling properties via the network of fibers.

In a still further aspect, the present disclosure provides a method of accelerating bone formation at an implantable tissue regeneration scaffold. In a still further aspect, the present disclosure provides a method of regenerating bone in a patient in need thereof, comprising implanting the patient with the implant.

In a still further aspect, the present disclosure provides a method of treating a bone defect caused by injury, disease, wounds, or surgery utilizing an implant comprising a combination of DBM fibers.

Kits

The present application also provides a medical kit for preparing the implant, or the disclosure for treating a patient, the kit including at least a delivery system comprising an electron beam irradiated medical implant as described above and a package enclosing the medical implant in a sterile condition. Such kits can include a dried material containing the solid ingredients of the composition along with an aqueous medium or other biocompatible wetting liquid for combination with the dried material to form a malleable wetted material, or can include the formulated, wetted malleable implant material in a suitable container such as a vial (e.g. terminally sterilized), and/or a therapeutic substance, for example an osteogenic substance such as a BMP. In one specific form, such a medical kit can include a dried material, such as a particulate or dried body, a BMP in lyophilized form (e.g., rhBMP-2), and an aqueous medium for reconstitution of the BMP to prepare an aqueous formulation that can then be added to the dried material in the process of preparing the implant of the disclosure.

The implant may have functional characteristics. Alternatively, other materials having functional characteristics may be incorporated into the implant. Functional characteristics may include radiopacity, bacteriocidity, source for released materials, tackiness, etc. Such characteristics may be imparted substantially throughout the implant or at only certain positions or portions of the implant.

Suitable radiopaque materials include, for example, ceramics, mineralized bone, ceramics/calcium phosphates/calcium sulfates, metal particles, fibers, and iodinated polymer. Suitable bacteriocidal materials may include, for example, trace metallic elements. In some embodiments, trace metallic elements may also encourage bone growth.

Functional material, such as radiopaque markers, may be provided at one or more locations on the coherent mass or may be provided substantially throughout the implant. Thus, for example, in a cylindrical implant, a radiopaque marker may be provided at a tip of the cylindrical implant. Such marker may facilitate placement of the implant. Radiopaque materials may be incorporated into the implant for delivery by the implant. Further, radiopaque materials may be provided at only some locations on the implant such that visualization of those locations provides indication of the orientation of the implant in vivo.

The implant of the disclosure can be used alone, as bone grafting materials, as scaffolds for bone tissue engineering for repair, augmentation and replacement of bone tissue or as carriers of growth factors, or carriers of genes.

Having now generally described the invention, the same may be more readily understood through the following reference to the following examples, which are provided by way of illustration and are not intended to limit the present invention unless specified.

EXAMPLES

The examples below with respect to certain formulations comprising GRAFTON® DBM DBF as the biologically active agent show that sterilization by e-beam irradiation has certain particularly advantageous results.

Example 1: 28 Day In Vivo Assessment of GRAFTON® DBM DBF Osteoinductivity Following Irradiation Twenty (20) finished units from ten (10) lots of GRAFTON® DBM DBF were used in this study. One unit from each lot was irradiated with e-beam (25 kGy, NuTek Corporation, Hayward, CA) while the second unit was only aseptically processed. All units were tested for osteoinductivity using the Rat Osteoinductive (OI) Assay described by Edwards et al (1998). Four replicates of each implant were placed in intermuscular sites in athymic rats for a period of 28 days. This bioassay has the ability to differentiate between the various levels of active (osteoinductive) demineralized bone preparations using histopathology assessments. To assess for donor-to-donor variability, each manufacturing lot corresponded to a different human tissue donor. Statistical analysis was performed using Minitab17 Statistical Software.

The results are summarized in FIG. 1. Results showed that the e-beam irradiation of GRAFTON® DBM DBF produced an average decrease of 14% in the osteoinductivity of the sample group evaluated (2.11±0.76 for the aseptic group vs 1.82±0.89 for the irradiated group). Thus, there is a slight decrease in osteoinductivity after e-beam irradiation by about 14% when compared to aseptic processing where no e-beam irradiation is used.

Figure 2A:
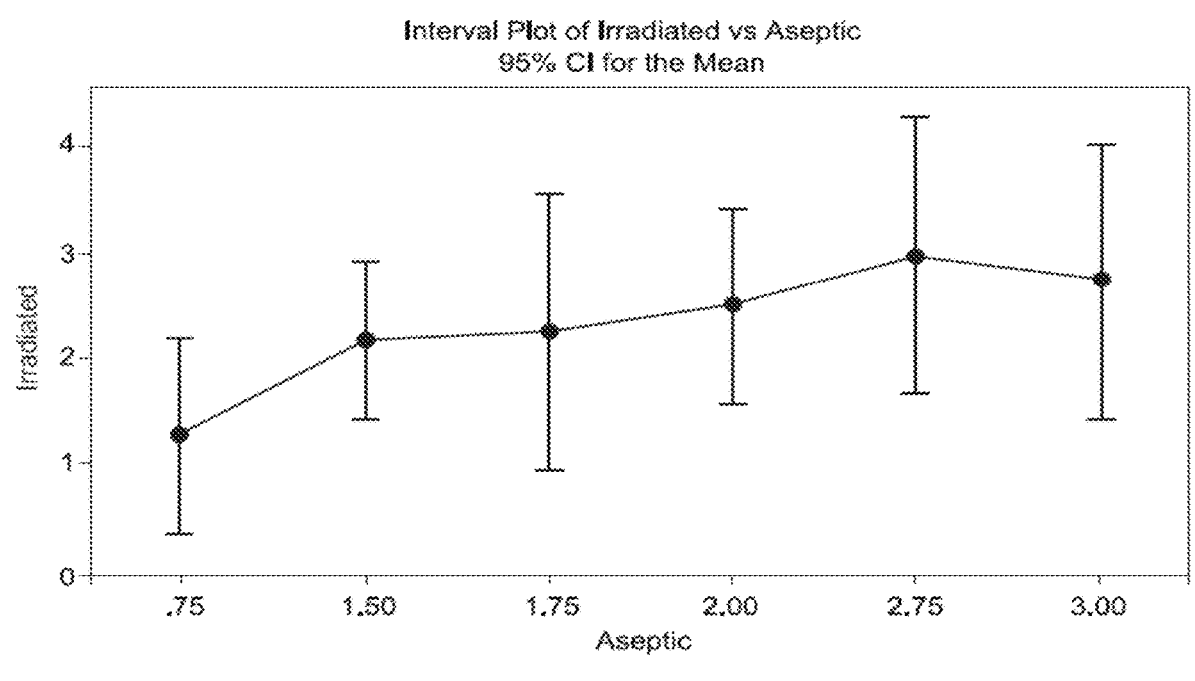
FIGS. 2A and 2B depict interval plots of irradiated aseptic samples. The pooled standard deviation was used to calculate the intervals. The 95% confidence interval (CI) was used for the mean.
Figure 2B:
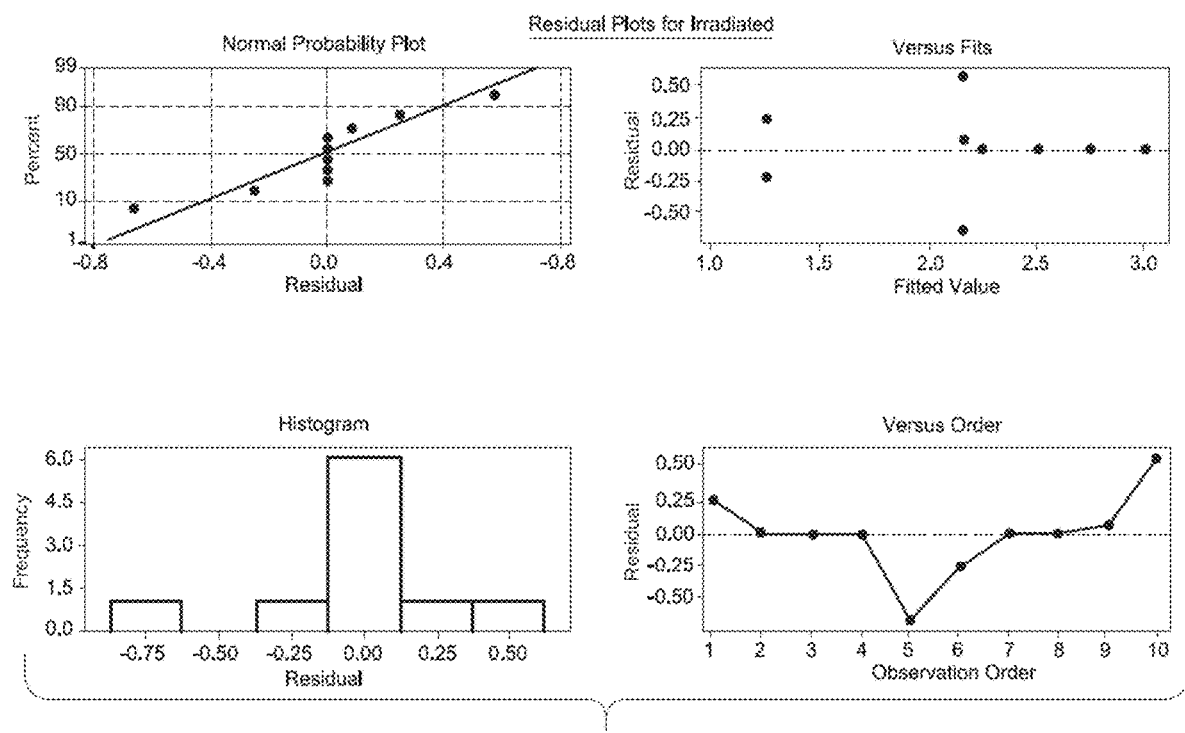

The irradiation of GRAFTON® DBM DBF did not result in a statistically significant decrease in osteoinductivity by ANOVA ($p=0.19$), and both units behaved with similar osteoinductivity. Using a confidence interval of 95% the standard deviation for this analysis was $S=0.25$; R-square=76.19%. FIG. 2A shows the residual plots for irradiated samples including a linear normal probability plot, fitted value plot, histogram, and observation order are summarized in FIG. 2B.

Example 2: Comparison of Osteoinductivity of e-Beam and Gamma Irradiated GRAFTON® DBM DBF with Non-Irradiated Controls Thirty six (36) finished units of GRAFTON® DBM DBF were used in this study. One unit from each lot was irradiated with e-beam (25 kGy, NuTek Corporation, Hayward, CA), or irradiated with gamma radiation, while the third unit was only aseptically processed and did not receive irradiation sterilization. All units were tested for osteoinductivity using the Rat Osteoinductive (OI) Assay described by Edwards et al (1998). Four replicates of each implant were placed in intermuscular sites in athymic rats for a period of 28 days. This bioassay has the ability to differentiate between the various levels of active (osteoinductive) demineralized bone preparations using histopathology assessments. To assess for donor-to-donor variability, each manufacturing lot corresponded to a different human tissue donor (n=3). Statistical analysis was performed using Minitab17 Statistical Software.

Figure 2C:
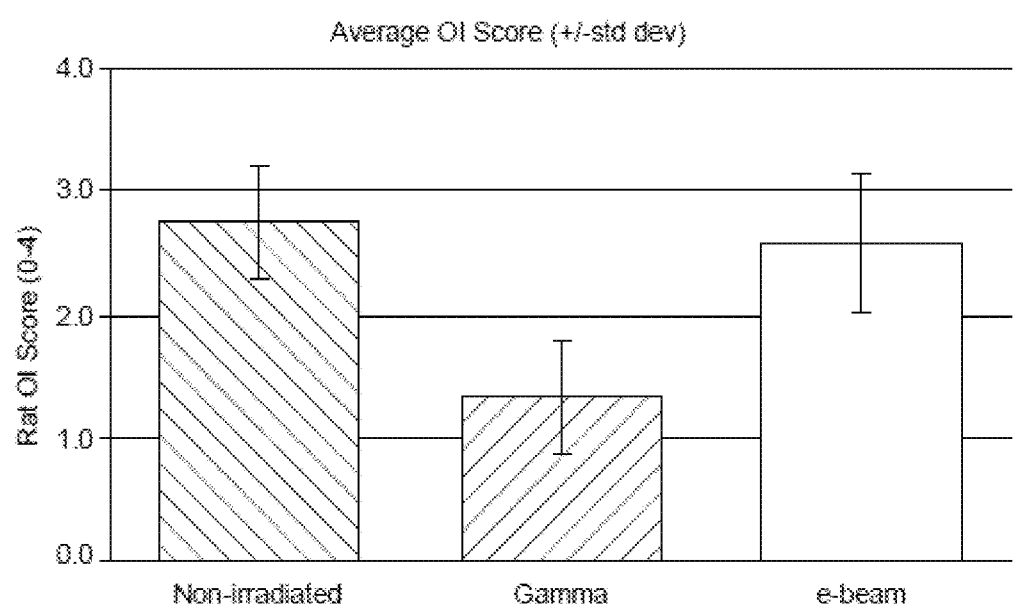
FIGS. 2C and 2D depict the effects of e-beam irradiation and gamma irradiation on the osteoinductivity of an osteoimplant in a rat.

The results are summarized in FIG. 2C and Table 1. Results showed that the e-beam irradiation of GRAFTON® DBM DBF produced an average decrease of 7.15% in the osteoinductivity of the sample group evaluated (2.8±0.5 for the non-irradiated group vs 2.6±0.5 for the e-beam irradiated group). Results showed that the Gamma irradiation of GRAFTON® DBM DBF produced an average decrease of 53.57% in the osteoinductivity of the sample group evaluated (2.8±0.5 for the non-irradiated group vs 1.3±0.5 for the gamma irradiated group).

Figure 2D:
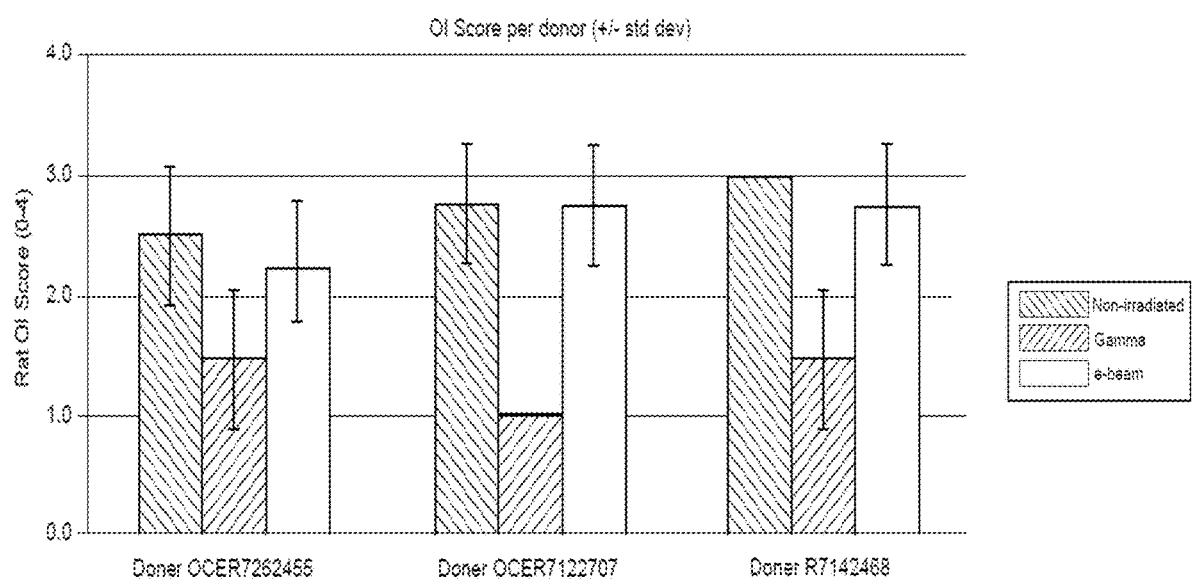

The e-beam irradiation of GRAFTON® DBM DBF did not result in a statistically significant decrease in osteoinductivity compared to non-irradiated samples ($p=0.41$, t-test), whereas gamma irradiation resulted in significantly reduced osteoinductivity ($p=2.5\times10^{-07}$, t-test). The results of individual OI scores per donor utilized for the above analysis are summarized in FIG. 2D and Table 2.

TABLE 1

| Donor | Average OI Score | | |
|---|---|---|---|
| | Non-irradiated | Gamma | e-beam |
| OCER7262455 | 3 | 1 | 3 |
| OCER7262455 | 2 | 2 | 2 |
| OCER7262455 | 3 | 1 | 2 |
| OCER7262455 | 2 | 2 | 2 |
| OCER7122707 | 3 | 1 | 3 |
| OCER7122707 | 3 | 1 | 3 |
| OCER7122707 | 2 | 1 | 3 |
| OCER7122707 | 3 | 1 | 2 |
| R7142468 | 3 | 2 | 3 |
| R7142468 | 3 | 1 | 3 |
| R7142468 | 3 | 1 | 2 |
| R7142468 | 3 | 2 | 3 |
| Average OI | 2.8 | 1.3 | 2.6 |
| Std. Dev. | 0.5 | 0.5 | 0.5 |
| t-test (compared to non-irradiated) | N/A | $2.5 \times 10^{-7}$ | 0.41 |

TABLE 2

OI Score per donor

| | Donor OCER7262455 | | | Donor OCER7122707 | | | Donor R7142468 | | |
|---|---|---|---|---|---|---|---|---|---|
| Replicate | Non-irradiated | Gamma | e-beam | Non-irradiated | Gamma | e-beam | Non-irradiated | Gamma | e-beam |
| 1 | 3 | 1 | 3 | 3 | 1 | 3 | 3 | 2 | 3 |
| 2 | 2 | 2 | 2 | 3 | 1 | 3 | 3 | 1 | 3 |
| 3 | 3 | 1 | 2 | 2 | 1 | 3 | 3 | 1 | 2 |
| 4 | 2 | 2 | 2 | 3 | 1 | 2 | 3 | 2 | 3 |
| Average | 2.5 | 1.5 | 2.3 | 2.8 | 1.0 | 2.8 | 3.0 | 1.5 | 2.8 |
| Std. Dev. | 0.6 | 0.6 | 0.5 | 0.5 | 0.0 | 0.5 | 0.0 | 0.6 | 0.5 |
| t-test | N/A | 0.050 | 0.54 | N/A | 0.0004 | 1.00 | N/A | 0.002 | 0.36 |

It should be understood that the forgoing relates to exemplary embodiments of the disclosure and that modifications may be made without departing from the spirit and scope of the disclosure as set forth in the following claims.

What is claimed is:

1. A method of treating a bone cavity, the method comprising:
providing an osteoinductive implant,
the osteoinductive implant being irradiated with electron beam radiation at a dose of from about 10 kilograys to 100 kilograys for a period of time to reduce microorganisms in the osteoinductive implant, the osteoinductive implant containing demineralized bone matrix (DBM) fibers having a length from about 1 to about 70 micrometers and being free of a carrier, wherein the electron beam irradiated osteoinductive implant retains at least about 80% osteoinductive properties; and
implanting the irradiated osteoinductive implant into the bone cavity.

2. A method of claim 1, wherein the method further comprises hydrating the irradiated osteoinductive implant with a liquid before implanting.

3. A method of claim 2, wherein after hydrating, the hydrated osteoinductive implant is formed into a putty or paste.

4. A method of claim 2, wherein the method further comprises molding the hydrated osteoinductive implant into a shape before implanting the osteoinductive implant.

5. A method of claim 2, wherein the osteoinductive implant is molded to conform to the bone cavity after it is hydrated.

6. A method of claim 1, wherein the osteoinductive properties of the irradiated osteoinductive implant are measured up to 6, 12, 18, 24, 32 or 36 months after storage at room temperature in a moisture barrier packaging.

7. A method of claim 1, wherein the electron beam irradiation reduces the microorganisms to a sterility assurance level (SAL) of about $10^{-6}$.

8. A method of claim 1, wherein the electron beam irradiation reduces microorganisms by 1-log reduction to 10-log reduction.

9. A method of claim 1, wherein the electron beam irradiated osteoinductive implant is hydrated by from about 1% to about 60% after it is irradiated.

10. A method of claim 9, wherein before the osteoinductive implant is hydrated, the irradiated osteoinductive implant comprises a low moisture content comprising less than 20%, 19%, 18%, 17%, 16%, 15%, 14%, 13%, 12%, 11%, 10%, 9%, 8%, 7%, 6%, 5%, 4%, 3%, 2%, or 1% moisture.

* * * * *